US010068248B2

(12) United States Patent
Knight et al.

(10) Patent No.: US 10,068,248 B2
(45) **Date of Patent: *Sep. 4, 2018**

(54) ANALYSIS OF CONTROLLED AND AUTOMATIC ATTENTION FOR INTRODUCTION OF STIMULUS MATERIAL

(71) Applicant: The Nielsen Company (US), LLC, New York, NY (US)

(72) Inventors: Robert T. Knight, Berkeley, CA (US); Ramachandran Gurumoorthy, Berkeley, CA (US); Anantha Pradeep, Berkeley, CA (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/299,752

(22) Filed: Oct. 21, 2016

(65) Prior Publication Data

US 2017/0039591 A1 Feb. 9, 2017

Related U.S. Application Data

(63) Continuation of application No. 12/608,660, filed on Oct. 29, 2009, now Pat. No. 9,560,984.

(51) Int. Cl.
*A61B 5/04* (2006.01)
*G06Q 30/02* (2012.01)
(Continued)

(52) U.S. Cl.
CPC ....... *G06Q 30/0244* (2013.01); *A61B 5/0484* (2013.01); *A61B 5/16* (2013.01); *G06Q 30/0269* (2013.01)

(58) Field of Classification Search
CPC ........... G06Q 30/0242; G06Q 30/0243; G06Q 30/0244; G06Q 30/0245; G06Q 30/0246;
(Continued)

(56) References Cited

U.S. PATENT DOCUMENTS

| | | | |
|---|---|---|---|
| 2,549,836 | A | 4/1951 | Mcintyre et al. |
| 3,490,439 | A | 1/1970 | Rolston |

(Continued)

FOREIGN PATENT DOCUMENTS

| | | |
|---|---|---|
| EP | 1087618 | 3/2001 |
| EP | 1609418 | 12/2005 |

(Continued)

OTHER PUBLICATIONS

Non-Final Office Action, issued by the United States Patent and Trademark Office in connection with U.S. Appl. No. 12/410,380, dated Jun. 17, 2016, 20 pages.

(Continued)

*Primary Examiner* — Jacqueline Cheng
*Assistant Examiner* — Eric Messersmith
(74) *Attorney, Agent, or Firm* — Hanley, Flight and Zimmerman, LLC

(57) ABSTRACT

A system analyzes neuro-response measurements including regional electroencephalography (EEG) measurements from subjects exposed to stimulus materials to determine locations in stimulus materials eliciting controlled attention and automatic attention. Additional stimulus materials are inserted into locations having salient attention attributes. In some examples, a challenging task is used to direct controlled attention onto a location and additional stimulus material is subtly presented in the location to benefit from automatic attention and salient attention measurements.

20 Claims, 8 Drawing Sheets

(51) Int. Cl.
*A61B 5/0484* (2006.01)
*A61B 5/16* (2006.01)

(58) Field of Classification Search
CPC .. G06Q 30/02; G06Q 30/0269; A61B 5/0484; A61B 5/16
See application file for complete search history.

(56) References Cited

U.S. PATENT DOCUMENTS 3,572,322 A 3/1971 Wade
3,735,753 A 5/1973 Pisarski
3,901,215 A 8/1975 John
3,998,213 A 12/1976 Price
4,075,657 A 2/1978 Weinblatt
4,145,122 A 3/1979 Rinard et al.
4,149,716 A 4/1979 Scudder
4,279,258 A 7/1981 John
4,411,273 A 10/1983 John
4,417,592 A 11/1983 John
4,537,198 A 8/1985 Corbett
4,557,270 A 12/1985 John
4,610,259 A 9/1986 Cohen et al.
4,613,951 A 9/1986 Chu
4,626,904 A 12/1986 Lurie
4,632,122 A 12/1986 Johansson et al.
4,683,892 A 8/1987 Johansson et al.
4,686,999 A 8/1987 Snyder et al.
4,695,879 A 9/1987 Weinblatt
4,736,751 A 4/1988 Gevins et al.
4,800,888 A 1/1989 Itil et al.
4,802,484 A 2/1989 Friedman et al.
4,846,190 A 7/1989 John
4,859,050 A 8/1989 Borah et al.
4,870,579 A 9/1989 Hey
4,885,687 A 12/1989 Carey
4,894,777 A 1/1990 Negishi et al.
4,913,160 A 4/1990 John
4,955,388 A 9/1990 Silberstein
4,967,038 A 10/1990 Gevins et al.
4,973,149 A 11/1990 Hutchinson
4,987,903 A 1/1991 Keppel et al.
5,003,986 A 4/1991 Finitzo et al.
5,010,891 A 4/1991 Chamoun
5,038,782 A 8/1991 Gevins et al.
5,083,571 A 1/1992 Prichep
RE34,015 E 8/1992 Duffy
5,137,027 A 8/1992 Rosenfeld
5,213,338 A 5/1993 Brotz
5,226,177 A 7/1993 Nickerson
5,243,517 A 9/1993 Schmidt et al.
5,273,037 A 12/1993 Itil et al.
5,291,888 A 3/1994 Tucker
5,293,867 A 3/1994 Oommen
5,295,491 A 3/1994 Gevins
5,331,544 A 7/1994 Taboada et al.
5,357,957 A 10/1994 Itil et al.
5,363,858 A 11/1994 Farwell
5,392,788 A 2/1995 Hudspeth
5,406,956 A 4/1995 Farwell
5,410,609 A 4/1995 Kado et al.
5,436,830 A 7/1995 Zaltman
5,447,166 A 9/1995 Gevins
5,474,082 A 12/1995 Junker
5,479,934 A 1/1996 Imran
5,513,649 A 5/1996 Gevins et al.
5,518,007 A 5/1996 Becker
5,537,618 A 7/1996 Boulton et al.
5,540,928 A 8/1996 Lu et al.
5,617,855 A 4/1997 Waletzky et al.
5,655,534 A 8/1997 Ilmoniemi
5,676,138 A 10/1997 Zawilinski
5,676,148 A 10/1997 Koo et al.
5,687,322 A 11/1997 Deaton et al.
5,720,619 A 2/1998 Fisslinger
5,724,987 A 3/1998 Gevins et al.
5,726,701 A 3/1998 Needham
5,729,205 A 3/1998 Kwon
5,736,986 A 4/1998 Sever, Jr.
5,740,035 A 4/1998 Cohen et al.
5,762,611 A 6/1998 Lewis et al.
5,771,897 A 6/1998 Zufrin
5,774,591 A 6/1998 Black et al.
5,787,187 A 7/1998 Bouchard et al.
5,800,351 A 9/1998 Mann
5,802,208 A 9/1998 Podilchuk et al.
5,802,220 A 9/1998 Black et al.
5,812,642 A 9/1998 Leroy
5,817,029 A 10/1998 Gevins et al.
5,842,199 A 11/1998 Miller et al.
5,848,399 A 12/1998 Burke
5,892,566 A 1/1999 Bullwinkel
5,945,863 A 8/1999 Coy
5,961,332 A 10/1999 Joao
5,974,262 A 10/1999 Fuller et al.
5,983,129 A * 11/1999 Cowan ............... A61B 5/04842 128/905
5,995,868 A 11/1999 Dorfmeister et al.
6,001,065 A 12/1999 DeVito
6,016,475 A 1/2000 Miller et al.
6,021,346 A 2/2000 Ryu et al.
6,032,129 A 2/2000 Greef et al.
6,052,619 A 4/2000 John
6,088,040 A 7/2000 Oda et al.
6,099,319 A 8/2000 Zaltman
6,120,440 A 9/2000 Goknar
6,128,521 A 10/2000 Marro et al.
6,154,669 A 11/2000 Hunter et al.
6,155,927 A 12/2000 Levasseur et al.
6,161,030 A 12/2000 Levendowski et al.
6,170,018 B1 1/2001 Voll et al.
6,171,239 B1 1/2001 Humphrey
6,173,260 B1 1/2001 Slaney
6,175,753 B1 1/2001 Menkes et al.
6,182,113 B1 1/2001 Narayanaswami
6,190,314 B1 2/2001 Ark et al.
6,212,502 B1 4/2001 Ball et al.
6,228,038 B1 5/2001 Claessens
6,236,885 B1 5/2001 Hunter et al.
6,236,975 B1 5/2001 Boe et al.
6,254,536 B1 7/2001 DeVito
6,280,198 B1 8/2001 Calhoun et al.
6,286,005 B1 9/2001 Cannon
6,289,234 B1 9/2001 Mueller
6,292,688 B1 9/2001 Patton
6,299,308 B1 10/2001 Voronka et al.
6,301,493 B1 10/2001 Marro et al.
6,315,569 B1 11/2001 Zaltman
6,330,470 B1 12/2001 Tucker et al.
6,334,778 B1 1/2002 Brown
6,358,201 B1 3/2002 Childre et al.
6,370,513 B1 4/2002 Kolawa et al.
6,374,143 B1 4/2002 Berrang et al.
6,381,481 B1 4/2002 Levendowski et al.
6,398,643 B1 6/2002 Knowles et al.
6,422,999 B1 7/2002 Hill
6,434,419 B1 8/2002 Gevins et al.
6,435,878 B1 8/2002 Reynolds et al.
6,453,194 B1 9/2002 Hill
6,453,241 B1 9/2002 Bassett, Jr. et al.
6,487,444 B2 11/2002 Mimura
6,488,617 B1 12/2002 Katz
6,510,340 B1 1/2003 Jordan
6,520,905 B1 2/2003 Surve et al.
6,545,685 B1 4/2003 Dorbie
6,575,902 B1 6/2003 Burton
6,577,329 B1 6/2003 Flickner et al.
6,585,521 B1 7/2003 Obrador
6,594,521 B2 7/2003 Tucker
6,598,006 B1 7/2003 Honda et al.
6,609,024 B1 8/2003 Ryu et al.
6,648,822 B2 11/2003 Hamamoto et al.
6,652,283 B1 11/2003 Van Schaack et al.
6,654,626 B2 11/2003 Devlin et al.
6,662,052 B1 12/2003 Sarwal et al.

(56) References Cited

U.S. PATENT DOCUMENTS

| | | | |
|---|---|---|---|
| 6,665,560 B2 | 12/2003 | Becker et al. | |
| 6,678,685 B2 | 1/2004 | McGill et al. | |
| 6,688,890 B2 | 2/2004 | Von Buegner | |
| 6,708,051 B1 | 3/2004 | Durousseau | |
| 6,712,468 B1 | 3/2004 | Edwards | |
| 6,754,524 B2 | 6/2004 | Johnson, Jr. | |
| 6,757,556 B2 | 6/2004 | Gopenathan et al. | |
| 6,788,882 B1 | 9/2004 | Geer et al. | |
| 6,792,304 B1 | 9/2004 | Silberstein | |
| 6,842,877 B2 | 1/2005 | Robarts et al. | |
| 6,850,252 B1 | 2/2005 | Hoffberg | |
| 6,852,875 B2 | 2/2005 | Prakash | |
| 6,888,457 B2 | 5/2005 | Wilkinson et al. | |
| 6,904,408 B1 | 6/2005 | McCarthy et al. | |
| 6,950,698 B2 | 9/2005 | Sarkela et al. | |
| 6,958,710 B2 | 10/2005 | Zhang et al. | |
| 6,973,342 B1 | 12/2005 | Swanson | |
| 6,993,380 B1 | 1/2006 | Modarres | |
| 7,020,508 B2 | 3/2006 | Stivoric et al. | |
| 7,043,056 B2 | 5/2006 | Edwards et al. | |
| 7,047,550 B1 | 5/2006 | Yasukawa et al. | |
| 7,113,916 B1 | 9/2006 | Hill | |
| 7,120,880 B1 | 10/2006 | Dryer et al. | |
| 7,130,673 B2 | 10/2006 | Tolvanen-Laakso et al. | |
| 7,150,715 B2 | 12/2006 | Collura et al. | |
| 7,164,967 B2 | 1/2007 | Etienne-Cummings et al. | |
| 7,177,675 B2 | 2/2007 | Suffin et al. | |
| 7,222,071 B2 | 5/2007 | Neuhauser et al. | |
| 7,246,081 B2 | 7/2007 | Hill | |
| 7,249,708 B2 | 7/2007 | McConnell et al. | |
| 7,272,982 B2 | 9/2007 | Neuhauser et al. | |
| 7,286,871 B2 | 10/2007 | Cohen | |
| 7,340,060 B2 | 3/2008 | Tomkins et al. | |
| 7,359,894 B1 | 4/2008 | Liebman et al. | |
| 7,391,835 B1 | 6/2008 | Gross et al. | |
| 7,394,385 B2 | 7/2008 | Franco, Jr. et al. | |
| 7,408,460 B2 | 8/2008 | Crystal et al. | |
| 7,420,464 B2 | 9/2008 | Fitzgerald et al. | |
| 7,443,292 B2 | 10/2008 | Jensen et al. | |
| 7,460,827 B2 | 12/2008 | Schuster et al. | |
| 7,463,143 B2 | 12/2008 | Forr et al. | |
| 7,463,144 B2 | 12/2008 | Crystal et al. | |
| 7,471,987 B2 | 12/2008 | Crystal et al. | |
| 7,483,835 B2 | 1/2009 | Neuhauser et al. | |
| 7,483,844 B2 | 1/2009 | Takakura et al. | |
| 7,496,400 B2 | 2/2009 | Hoskonen et al. | |
| 7,548,774 B2 | 6/2009 | Kurtz et al. | |
| 7,551,952 B2 | 6/2009 | Gevins et al. | |
| 7,592,908 B2 | 9/2009 | Zhang et al. | |
| 7,614,066 B2 | 11/2009 | Urdang et al. | |
| 7,623,823 B2 | 11/2009 | Zito et al. | |
| 7,630,757 B2 | 12/2009 | Dorfmeister et al. | |
| 7,636,456 B2 | 12/2009 | Collins et al. | |
| 7,650,793 B2 | 1/2010 | Jensen et al. | |
| 7,658,327 B2 | 2/2010 | Tuclnnan et al. | |
| 7,689,272 B2 | 3/2010 | Farwell | |
| 7,697,979 B2 | 4/2010 | Martinerie et al. | |
| 7,698,238 B2 | 4/2010 | Barletta et al. | |
| 7,720,351 B2 | 5/2010 | Levitan | |
| 7,729,755 B2 | 5/2010 | Laken | |
| 7,765,564 B2 | 7/2010 | Deng | |
| 7,774,052 B2 | 8/2010 | Burton et al. | |
| 7,797,186 B2 | 9/2010 | Dybus | |
| 7,809,420 B2 | 10/2010 | Hannula et al. | |
| 7,840,248 B2 | 11/2010 | Fuchs et al. | |
| 7,840,250 B2 | 11/2010 | Tucker | |
| 7,844,484 B2 | 11/2010 | Arnett et al. | |
| 7,865,394 B1 | 1/2011 | Calloway | |
| 7,892,764 B2 | 2/2011 | Xiong et al. | |
| 7,895,075 B2 | 2/2011 | Gettys et al. | |
| 7,895,625 B1 | 2/2011 | Bryan et al. | |
| 7,908,133 B2 | 3/2011 | Neuhauser | |
| 7,917,366 B1 | 3/2011 | Levanon et al. | |
| 7,930,199 B1 | 4/2011 | Hill | |
| 7,962,315 B2 | 6/2011 | Jensen et al. | |
| 7,974,889 B2 | 7/2011 | Raimbeault | |
| 7,988,557 B2 | 8/2011 | Soderland | |
| 8,014,847 B2 | 9/2011 | Shastri et al. | |
| 8,027,518 B2 | 9/2011 | Baker et al. | |
| 8,060,795 B2 | 11/2011 | Bakekolo et al. | |
| 8,065,203 B1 | 11/2011 | Chien et al. | |
| 8,069,125 B2 | 11/2011 | Jung et al. | |
| 8,073,707 B2 | 12/2011 | Teller et al. | |
| 8,079,054 B1 * | 12/2011 | Dhawan | G06Q 30/00 705/14.4 |
| 8,082,215 B2 | 12/2011 | Jung et al. | |
| 8,086,563 B2 | 12/2011 | Jung et al. | |
| 8,098,152 B2 | 1/2012 | Zhang et al. | |
| 8,099,315 B2 | 1/2012 | Amento et al. | |
| 8,103,328 B2 | 1/2012 | Turner et al. | |
| 8,126,220 B2 | 2/2012 | Greig | |
| 8,135,606 B2 | 3/2012 | Dupree | |
| 8,151,298 B2 | 4/2012 | Begeja et al. | |
| 8,165,916 B2 | 4/2012 | Hoffberg et al. | |
| 8,196,168 B1 | 6/2012 | Bryan et al. | |
| 8,200,775 B2 | 6/2012 | Moore | |
| 8,209,224 B2 | 6/2012 | Pradeep et al. | |
| 8,229,469 B2 | 7/2012 | Zhang et al. | |
| 8,235,725 B1 | 7/2012 | Hill | |
| 8,255,267 B2 | 8/2012 | Breiter | |
| 8,270,814 B2 | 9/2012 | Pradeep et al. | |
| 8,296,172 B2 | 10/2012 | Marci et al. | |
| 8,300,526 B2 | 10/2012 | Saito et al. | |
| 8,326,002 B2 | 12/2012 | Hill | |
| 8,327,395 B2 | 12/2012 | Lee | |
| 8,332,883 B2 | 12/2012 | Lee | |
| 8,335,715 B2 | 12/2012 | Pradeep et al. | |
| 8,381,244 B2 | 2/2013 | King | |
| 8,386,312 B2 | 2/2013 | Pradeep et al. | |
| 8,386,313 B2 | 2/2013 | Pradeep et al. | |
| 8,388,165 B2 | 3/2013 | Zhang | |
| 8,392,250 B2 | 3/2013 | Pradeep et al. | |
| 8,392,251 B2 | 3/2013 | Pradeep et al. | |
| 8,392,253 B2 | 3/2013 | Pradeep et al. | |
| 8,392,254 B2 | 3/2013 | Pradeep et al. | |
| 8,392,255 B2 | 3/2013 | Pradeep et al. | |
| 8,396,744 B2 | 3/2013 | Pradeep et al. | |
| 8,473,345 B2 | 6/2013 | Pradeep et al. | |
| 8,484,801 B2 | 7/2013 | Pradeep et al. | |
| 8,494,610 B2 | 7/2013 | Pradeep et al. | |
| 8,494,905 B2 | 7/2013 | Pradeep et al. | |
| 8,533,042 B2 | 9/2013 | Pradeep et al. | |
| 8,548,852 B2 | 10/2013 | Pradeep et al. | |
| 8,561,095 B2 | 10/2013 | Dimitrova et al. | |
| 8,600,100 B2 | 12/2013 | Hill | |
| 8,635,105 B2 | 1/2014 | Pradeep et al. | |
| 8,655,428 B2 | 2/2014 | Pradeep et al. | |
| 8,655,437 B2 | 2/2014 | Pradeep et al. | |
| 8,764,652 B2 | 7/2014 | Lee et al. | |
| 8,788,372 B2 | 7/2014 | Kettner et al. | |
| 8,793,715 B1 | 7/2014 | Weitzenfeld et al. | |
| 9,021,515 B2 | 4/2015 | Lee et al. | |
| 9,336,535 B2 | 5/2016 | Pradeep et al. | |
| 9,560,984 B2 | 2/2017 | Pradeep et al. | |
| 2001/0013009 A1 | 8/2001 | Greening et al. | |
| 2001/0020236 A1 | 9/2001 | Cannon | |
| 2001/0029468 A1 | 10/2001 | Yamaguchi et al. | |
| 2001/0032140 A1 | 10/2001 | Hoffman | |
| 2001/0056225 A1 | 12/2001 | DeVito | |
| 2002/0053076 A1 | 5/2002 | Landesmann | |
| 2002/0055857 A1 | 5/2002 | Mault | |
| 2002/0056087 A1 | 5/2002 | Berezowski et al. | |
| 2002/0056124 A1 | 5/2002 | Hay | |
| 2002/0059577 A1 | 5/2002 | Lu et al. | |
| 2002/0065826 A1 | 5/2002 | Bell et al. | |
| 2002/0072952 A1 | 6/2002 | Hamzey et al. | |
| 2002/0077534 A1 | 6/2002 | DuRousseau | |
| 2002/0082902 A1 | 6/2002 | Ando et al. | |
| 2002/0103429 A1 | 8/2002 | deCharms | |
| 2002/0111796 A1 | 8/2002 | Nemoto | |
| 2002/0143627 A1 | 10/2002 | Barsade et al. | |
| 2002/0155878 A1 | 10/2002 | Lert, Jr. et al. | |
| 2002/0156842 A1 | 10/2002 | Signes et al. | |
| 2002/0169665 A1 | 11/2002 | Hughes et al. | |

(56) References Cited

U.S. PATENT DOCUMENTS

| | | | |
|---|---|---|---|
| 2002/0188216 | A1 | 12/2002 | Kayyali et al. |
| 2002/0188217 | A1 | 12/2002 | Farwell |
| 2002/0193670 | A1 | 12/2002 | Garfield et al. |
| 2003/0013981 | A1 | 1/2003 | Gevins et al. |
| 2003/0036955 | A1 | 2/2003 | Tanaka et al. |
| 2003/0037333 | A1 | 2/2003 | Ghashghai et al. |
| 2003/0044050 | A1 | 3/2003 | Clark et al. |
| 2003/0059750 | A1 | 3/2003 | Bindler et al. |
| 2003/0063222 | A1 | 4/2003 | Creed et al. |
| 2003/0065524 | A1 | 4/2003 | Giacchetti et al. |
| 2003/0081834 | A1 | 5/2003 | Philomin et al. |
| 2003/0093792 | A1 | 5/2003 | Labeeb et al. |
| 2003/0100998 | A2 | 5/2003 | Bnumer et al. |
| 2003/0104865 | A1 | 6/2003 | Itkis et al. |
| 2003/0131351 | A1 | 7/2003 | Shapira |
| 2003/0149344 | A1 | 8/2003 | Nizan |
| 2003/0165270 | A1 | 9/2003 | Endrikhovski et al. |
| 2003/0177488 | A1 | 9/2003 | Smith et al. |
| 2003/0204412 | A1 | 10/2003 | Brier |
| 2003/0208754 | A1 | 11/2003 | Sridhar et al. |
| 2003/0233278 | A1 | 12/2003 | Marshall |
| 2004/0001616 | A1 | 1/2004 | Gutta et al. |
| 2004/0005143 | A1 | 1/2004 | Tsuru et al. |
| 2004/0013398 | A1 | 1/2004 | Miura et al. |
| 2004/0015608 | A1 | 1/2004 | Ellis et al. |
| 2004/0055448 | A1 | 3/2004 | Byon |
| 2004/0068431 | A1 | 4/2004 | Smith et al. |
| 2004/0073129 | A1 | 4/2004 | Caldwell et al. |
| 2004/0092809 | A1 | 5/2004 | De Charms |
| 2004/0098298 | A1 | 5/2004 | Yin |
| 2004/0101212 | A1 | 5/2004 | Fedorovskaya et al. |
| 2004/0133081 | A1 | 7/2004 | Teller et al. |
| 2004/0187167 | A1 | 9/2004 | Maguire et al. |
| 2004/0193068 | A1 | 9/2004 | Burton et al. |
| 2004/0210159 | A1 | 10/2004 | Kibar et al. |
| 2004/0219184 | A1 | 11/2004 | Brown et al. |
| 2004/0220483 | A1 | 11/2004 | Yeo et al. |
| 2004/0236623 | A1 | 11/2004 | Gopalakrishnan |
| 2005/0010475 | A1 | 1/2005 | Perkowski et al. |
| 2005/0041951 | A1 | 2/2005 | Inoue et al. |
| 2005/0043646 | A1 | 2/2005 | Virre et al. |
| 2005/0060312 | A1 | 2/2005 | Curtiss et al. |
| 2005/0062637 | A1 | 3/2005 | El Zabadani et al. |
| 2005/0071462 | A1 | 3/2005 | Bodin et al. |
| 2005/0071865 | A1 | 3/2005 | Martins |
| 2005/0076359 | A1 | 4/2005 | Pierson et al. |
| 2005/0079474 | A1 | 4/2005 | Lowe |
| 2005/0097594 | A1 | 5/2005 | O'Donnell et al. |
| 2005/0107716 | A1 | 5/2005 | Eaton et al. |
| 2005/0113649 | A1 | 5/2005 | Bergantino |
| 2005/0132401 | A1 | 6/2005 | Boccon-Gibod et al. |
| 2005/0143629 | A1 | 6/2005 | Farwell |
| 2005/0149964 | A1 | 7/2005 | Thomas et al. |
| 2005/0154290 | A1 | 7/2005 | Langleben |
| 2005/0177058 | A1 | 8/2005 | Sobell |
| 2005/0197590 | A1 | 9/2005 | Osorio et al. |
| 2005/0203798 | A1 | 9/2005 | Jensen et al. |
| 2005/0216243 | A1 | 9/2005 | Graham et al. |
| 2005/0223237 | A1 | 10/2005 | Barletta et al. |
| 2005/0227233 | A1 | 10/2005 | Buxton et al. |
| 2005/0240956 | A1 | 10/2005 | Smith et al. |
| 2005/0256905 | A1 | 11/2005 | Gruhl et al. |
| 2005/0261980 | A1 | 11/2005 | Hadi |
| 2005/0267798 | A1 | 12/2005 | Panara |
| 2005/0272017 | A1 | 12/2005 | Neuhauser et al. |
| 2005/0273017 | A1 | 12/2005 | Gordon |
| 2005/0273802 | A1 | 12/2005 | Crystal et al. |
| 2005/0288954 | A1 | 12/2005 | McCarthy et al. |
| 2005/0289582 | A1 | 12/2005 | Tavares et al. |
| 2006/0003732 | A1 | 1/2006 | Neuhauser et al. |
| 2006/0009702 | A1 | 1/2006 | Iwaki et al. |
| 2006/0010470 | A1 | 1/2006 | Kurosaki |
| 2006/0035707 | A1 | 2/2006 | Nguyen et al. |
| 2006/0041548 | A1 | 2/2006 | Parsons et al. |
| 2006/0042483 | A1 | 3/2006 | Work et al. |
| 2006/0053110 | A1 | 3/2006 | McDonald et al. |
| 2006/0069663 | A1 | 3/2006 | Adar et al. |
| 2006/0093998 | A1 | 5/2006 | Vertegaal |
| 2006/0111044 | A1 | 5/2006 | Keller |
| 2006/0111644 | A1 | 5/2006 | Guttag et al. |
| 2006/0129458 | A1 | 6/2006 | Maggio |
| 2006/0167376 | A1 | 7/2006 | Viirre et al. |
| 2006/0168613 | A1 | 7/2006 | Wood et al. |
| 2006/0168630 | A1 | 7/2006 | Davies |
| 2006/0176289 | A1 | 8/2006 | Horn |
| 2006/0190822 | A1 | 8/2006 | Basson et al. |
| 2006/0218046 | A1 | 9/2006 | Carfi et al. |
| 2006/0256133 | A1 | 11/2006 | Rosenberg |
| 2006/0257834 | A1 | 11/2006 | Lee et al. |
| 2006/0259360 | A1 | 11/2006 | Flinn et al. |
| 2006/0259371 | A1 | 11/2006 | Perrier et al. |
| 2006/0293921 | A1 | 12/2006 | McCarthy et al. |
| 2007/0016096 | A1 | 1/2007 | McNabb |
| 2007/0038516 | A1 | 2/2007 | Apple et al. |
| 2007/0048707 | A1 | 3/2007 | Caamano et al. |
| 2007/0050256 | A1 | 3/2007 | Walker et al. |
| 2007/0055169 | A1 | 3/2007 | Lee et al. |
| 2007/0060830 | A1 | 3/2007 | Le et al. |
| 2007/0060831 | A1 | 3/2007 | Le et al. |
| 2007/0066874 | A1 | 3/2007 | Cook |
| 2007/0066915 | A1 | 3/2007 | Frei et al. |
| 2007/0066916 | A1 | 3/2007 | Lemos |
| 2007/0067007 | A1 | 3/2007 | Schulman et al. |
| 2007/0067305 | A1 | 3/2007 | Ives |
| 2007/0078700 | A1 | 4/2007 | Lenzmann et al. |
| 2007/0078706 | A1 | 4/2007 | Datta et al. |
| 2007/0079331 | A1 | 4/2007 | Datta et al. |
| 2007/0101360 | A1 | 5/2007 | Gutta et al. |
| 2007/0106170 | A1 | 5/2007 | Dunseath, Jr. et al. |
| 2007/0112460 | A1 | 5/2007 | Kiselik |
| 2007/0135727 | A1 | 6/2007 | Virtanen et al. |
| 2007/0135728 | A1 | 6/2007 | Snyder et al. |
| 2007/0136753 | A1 | 6/2007 | Bovenschulte et al. |
| 2007/0150916 | A1 | 6/2007 | Begole et al. |
| 2007/0209047 | A1 | 9/2007 | Hallberg et al. |
| 2007/0214471 | A1 | 9/2007 | Rosenberg |
| 2007/0225585 | A1 | 9/2007 | Washbon et al. |
| 2007/0225674 | A1 | 9/2007 | Molnar et al. |
| 2007/0226760 | A1 | 9/2007 | Neuhauser et al. |
| 2007/0235716 | A1 | 10/2007 | Delic et al. |
| 2007/0238945 | A1 | 10/2007 | Delic et al. |
| 2007/0250846 | A1 | 10/2007 | Swix et al. |
| 2007/0250901 | A1 | 10/2007 | McIntire et al. |
| 2007/0265507 | A1 | 11/2007 | de Lemos |
| 2007/0282566 | A1 | 12/2007 | Whitlow et al. |
| 2007/0294132 | A1 | 12/2007 | Zhang et al. |
| 2007/0294705 | A1 | 12/2007 | Gopalakrishnan |
| 2007/0294706 | A1 | 12/2007 | Neuhauser et al. |
| 2008/0001600 | A1 | 1/2008 | deC harms |
| 2008/0004940 | A1 | 1/2008 | Rolleston Phillips |
| 2008/0010110 | A1 | 1/2008 | Neuhauser et al. |
| 2008/0027345 | A1 | 1/2008 | Kumada et al. |
| 2008/0040740 | A1 | 2/2008 | Plotnick et al. |
| 2008/0059997 | A1 | 3/2008 | Plotnick et al. |
| 2008/0065468 | A1 | 3/2008 | Berget al. |
| 2008/0065721 | A1 | 3/2008 | Cragun |
| 2008/0081961 | A1 | 4/2008 | Westbrook et al. |
| 2008/0082019 | A1 | 4/2008 | Ludving et al. |
| 2008/0086356 | A1 | 4/2008 | Glassman et al. |
| 2008/0091463 | A1 | 4/2008 | Shakamuri |
| 2008/0091512 | A1 | 4/2008 | Marci et al. |
| 2008/0097854 | A1 | 4/2008 | Young |
| 2008/0109840 | A1 | 5/2008 | Walter et al. |
| 2008/0125110 | A1 | 5/2008 | Ritter |
| 2008/0133724 | A1 | 6/2008 | Clark |
| 2008/0147448 | A1 | 6/2008 | Tunick et al. |
| 2008/0147742 | A1 | 6/2008 | Allen |
| 2008/0152300 | A1 | 6/2008 | Knee et al. |
| 2008/0162182 | A1 | 7/2008 | Cazares et al. |
| 2008/0177197 | A1 | 7/2008 | Lee et al. |
| 2008/0195471 | A1 | 8/2008 | Dube |
| 2008/0204273 | A1 | 8/2008 | Crystal et al. |
| 2008/0208072 | A1 | 8/2008 | Fadem et al. |
| 2008/0214902 | A1 | 9/2008 | Lee et al. |

(56) References Cited

U.S. PATENT DOCUMENTS

| | | | |
|---|---|---|---|
| 2008/0218472 | A1 | 9/2008 | Breen et al. |
| 2008/0221400 | A1 | 9/2008 | Lee et al. |
| 2008/0221472 | A1 | 9/2008 | Lee et al. |
| 2008/0221969 | A1 | 9/2008 | Lee et al. |
| 2008/0222670 | A1 | 9/2008 | Lee et al. |
| 2008/0222671 | A1 | 9/2008 | Lee et al. |
| 2008/0228077 | A1 | 9/2008 | Wilk et al. |
| 2008/0249865 | A1 | 10/2008 | Angell et al. |
| 2008/0255949 | A1 | 10/2008 | Genco et al. |
| 2008/0295126 | A1 | 11/2008 | Lee et al. |
| 2008/0306398 | A1 | 12/2008 | Uchiyama et al. |
| 2009/0018996 | A1 | 1/2009 | Hunt et al. |
| 2009/0024049 | A1 | 1/2009 | Pradeep et al. |
| 2009/0024447 | A1 | 1/2009 | Pradeep et al. |
| 2009/0024448 | A1 | 1/2009 | Pradeep et al. |
| 2009/0024449 | A1 | 1/2009 | Pradeep et al. |
| 2009/0024475 | A1 | 1/2009 | Pradeep et al. |
| 2009/0024747 | A1 | 1/2009 | Moses et al. |
| 2009/0025023 | A1 | 1/2009 | Pradeep et al. |
| 2009/0025024 | A1 | 1/2009 | Beser et al. |
| 2009/0030287 | A1 | 1/2009 | Pradeep et al. |
| 2009/0030303 | A1 | 1/2009 | Pradeep et al. |
| 2009/0030717 | A1 | 1/2009 | Pradeep et al. |
| 2009/0030762 | A1 | 1/2009 | Lee et al. |
| 2009/0030780 | A1 | 1/2009 | York et al. |
| 2009/0030930 | A1 | 1/2009 | Pradeep et al. |
| 2009/0036755 | A1 | 2/2009 | Pradeep et al. |
| 2009/0036756 | A1 | 2/2009 | Pradeep et al. |
| 2009/0037575 | A1 | 2/2009 | Crystal et al. |
| 2009/0060240 | A1 | 3/2009 | Coughlan et al. |
| 2009/0062629 | A1 | 3/2009 | Pradeep et al. |
| 2009/0062679 | A1 | 3/2009 | Tan et al. |
| 2009/0062680 | A1 | 3/2009 | Sandford |
| 2009/0062681 | A1 | 3/2009 | Pradeep et al. |
| 2009/0063255 | A1 | 3/2009 | Pradeep et al. |
| 2009/0063256 | A1 | 3/2009 | Pradeep et al. |
| 2009/0069652 | A1 | 3/2009 | Lee et al. |
| 2009/0070798 | A1 | 3/2009 | Lee et al. |
| 2009/0082643 | A1 | 3/2009 | Pradeep et al. |
| 2009/0082689 | A1 | 3/2009 | Guttag et al. |
| 2009/0082692 | A1 | 3/2009 | Hale et al. |
| 2009/0083129 | A1 | 3/2009 | Pradeep et al. |
| 2009/0088610 | A1 | 4/2009 | Lee et al. |
| 2009/0089830 | A1 | 4/2009 | Chandratillake et al. |
| 2009/0094286 | A1 | 4/2009 | Lee et al. |
| 2009/0094627 | A1 | 4/2009 | Lee et al. |
| 2009/0094628 | A1 | 4/2009 | Lee et al. |
| 2009/0094629 | A1 | 4/2009 | Lee et al. |
| 2009/0097689 | A1 | 4/2009 | Prest et al. |
| 2009/0099873 | A1 | 4/2009 | Kurple |
| 2009/0112077 | A1 | 4/2009 | Nguyen et al. |
| 2009/0112117 | A1 | 4/2009 | Rewari |
| 2009/0119154 | A1 | 5/2009 | Jung et al. |
| 2009/0131764 | A1 | 5/2009 | Lee et al. |
| 2009/0132441 | A1 | 5/2009 | Muller et al. |
| 2009/0133047 | A1 | 5/2009 | Lee et al. |
| 2009/0138356 | A1 | 5/2009 | Pomplun |
| 2009/0144780 | A1 | 6/2009 | Toebes et al. |
| 2009/0150919 | A1 | 6/2009 | Lee et al. |
| 2009/0150920 | A1 | 6/2009 | Jones |
| 2009/0153328 | A1 | 6/2009 | Otani et al. |
| 2009/0156907 | A1 | 6/2009 | Jung et al. |
| 2009/0156955 | A1 | 6/2009 | Jung et al. |
| 2009/0158308 | A1 | 6/2009 | Weitzenfeld et al. |
| 2009/0163777 | A1 | 6/2009 | Jung et al. |
| 2009/0164132 | A1 | 6/2009 | Jung et al. |
| 2009/0171164 | A1 | 7/2009 | Jung et al. |
| 2009/0187467 | A1 | 7/2009 | Fang et al. |
| 2009/0195392 | A1 | 8/2009 | Zalewsld |
| 2009/0214060 | A1 | 8/2009 | Chuang et al. |
| 2009/0216611 | A1 | 8/2009 | Leonard et al. |
| 2009/0221928 | A1 | 9/2009 | Einav et al. |
| 2009/0248484 | A1 | 10/2009 | Surendran et al. |
| 2009/0248496 | A1 | 10/2009 | Hueter et al. |
| 2009/0248594 | A1 | 10/2009 | Castleman et al. |
| 2009/0249223 | A1 | 10/2009 | Barsook et al. |
| 2009/0253996 | A1 | 10/2009 | Lee et al. |
| 2009/0259137 | A1 | 10/2009 | Delic et al. |
| 2009/0259509 | A1 | 10/2009 | Landvater |
| 2009/0271294 | A1 | 10/2009 | Hadi |
| 2009/0287108 | A1 | 11/2009 | Levy |
| 2009/0292587 | A1 | 11/2009 | Fitzgerald |
| 2009/0300672 | A1 | 12/2009 | Van Gulik |
| 2009/0305006 | A1 | 12/2009 | Steffen |
| 2009/0318773 | A1 | 12/2009 | Jung et al. |
| 2009/0318826 | A1 | 12/2009 | Green et al. |
| 2009/0327068 | A1 | 12/2009 | Pradeep et al. |
| 2009/0328089 | A1 | 12/2009 | Pradeep et al. |
| 2009/0328122 | A1 | 12/2009 | Amento et al. |
| 2010/0004977 | A1 | 1/2010 | Marci et al. |
| 2010/0022821 | A1 | 1/2010 | Dubi et al. |
| 2010/0041962 | A1 | 2/2010 | Causevic et al. |
| 2010/0042012 | A1 | 2/2010 | Alhussiny |
| 2010/0060300 | A1 | 3/2010 | Muller et al. |
| 2010/0094702 | A1* | 4/2010 | Silberstein ......... A61B 5/04012 705/14.43 |
| 2010/0121716 | A1 | 5/2010 | Golan |
| 2010/0125219 | A1 | 5/2010 | Harris et al. |
| 2010/0145176 | A1 | 6/2010 | Himes |
| 2010/0145215 | A1 | 6/2010 | Pradeep et al. |
| 2010/0145217 | A1 | 6/2010 | Otto et al. |
| 2010/0153175 | A1 | 6/2010 | Pearson et al. |
| 2010/0169153 | A1 | 7/2010 | Hwacinski et al. |
| 2010/0169162 | A1 | 7/2010 | Anderson et al. |
| 2010/0179881 | A1 | 7/2010 | Wiederstein |
| 2010/0180029 | A1 | 7/2010 | Fourman |
| 2010/0183279 | A1 | 7/2010 | Pradeep et al. |
| 2010/0186031 | A1 | 7/2010 | Pradeep et al. |
| 2010/0186032 | A1 | 7/2010 | Pradeep et al. |
| 2010/0198042 | A1 | 8/2010 | Popescu et al. |
| 2010/0211439 | A1 | 8/2010 | Marci et al. |
| 2010/0214318 | A1 | 8/2010 | Pradeep et al. |
| 2010/0215289 | A1 | 8/2010 | Pradeep et al. |
| 2010/0218208 | A1 | 8/2010 | Holden |
| 2010/0223094 | A1 | 9/2010 | Cumming et al. |
| 2010/0228604 | A1 | 9/2010 | Desai et al. |
| 2010/0228614 | A1 | 9/2010 | Zhang et al. |
| 2010/0234752 | A1 | 9/2010 | Sullivan et al. |
| 2010/0241580 | A1 | 9/2010 | Schleier-Smith |
| 2010/0249538 | A1 | 9/2010 | Pradeep et al. |
| 2010/0249636 | A1 | 9/2010 | Pradeep et al. |
| 2010/0250325 | A1 | 9/2010 | Pradeep et al. |
| 2010/0250347 | A1 | 9/2010 | Rainer et al. |
| 2010/0250458 | A1 | 9/2010 | Ho |
| 2010/0257052 | A1 | 10/2010 | Zito |
| 2010/0263005 | A1 | 10/2010 | White |
| 2010/0268540 | A1 | 10/2010 | Arshi et al. |
| 2010/0268573 | A1 | 10/2010 | Jain et al. |
| 2010/0268720 | A1 | 10/2010 | Spivack et al. |
| 2010/0269127 | A1 | 10/2010 | Krug |
| 2010/0274152 | A1 | 10/2010 | McPeck et al. |
| 2010/0287152 | A1 | 11/2010 | Hauser |
| 2010/0292998 | A1 | 11/2010 | Bodlaender et al. |
| 2010/0306030 | A1 | 12/2010 | Mawani |
| 2010/0306120 | A1 | 12/2010 | Ciptawilangga |
| 2010/0317988 | A1 | 12/2010 | Terada et al. |
| 2010/0318507 | A1 | 12/2010 | Grant et al. |
| 2010/0325660 | A1 | 12/2010 | Holden |
| 2010/0331661 | A1 | 12/2010 | Nakagawa |
| 2011/0004089 | A1 | 1/2011 | Chou |
| 2011/0015503 | A1 | 1/2011 | Joffe et al. |
| 2011/0020778 | A1 | 1/2011 | Forbes |
| 2011/0022965 | A1 | 1/2011 | Lawerence et al. |
| 2011/0040155 | A1 | 2/2011 | Guzak et al. |
| 2011/0040202 | A1 | 2/2011 | Luo et al. |
| 2011/0043759 | A1 | 2/2011 | Bushinski |
| 2011/0046473 | A1 | 2/2011 | Pradeep et al. |
| 2011/0046502 | A1 | 2/2011 | Pradeep et al. |
| 2011/0046503 | A1 | 2/2011 | Pradeep et al. |
| 2011/0046504 | A1 | 2/2011 | Pradeep et al. |
| 2011/0047035 | A1 | 2/2011 | Gidwani et al. |
| 2011/0047121 | A1 | 2/2011 | Pradeep et al. |
| 2011/0059422 | A1 | 3/2011 | Masaoka |
| 2011/0071874 | A1 | 3/2011 | Schneersohn et al. |

(56) References Cited

U.S. PATENT DOCUMENTS

| | | | |
|---|---|---|---|
| 2011/0076942 | A1 | 3/2011 | Taveau et al. |
| 2011/0084795 | A1 | 4/2011 | Fukuyori |
| 2011/0085700 | A1 | 4/2011 | Lee |
| 2011/0098593 | A1 | 4/2011 | Low et al. |
| 2011/0105937 | A1 | 5/2011 | Pradeep et al. |
| 2011/0106621 | A1 | 5/2011 | Pradeep et al. |
| 2011/0106750 | A1 | 5/2011 | Pradeep et al. |
| 2011/0119124 | A1 | 5/2011 | Pradeep et al. |
| 2011/0119129 | A1 | 5/2011 | Pradeep et al. |
| 2011/0119130 | A1 | 5/2011 | Agan et al. |
| 2011/0153390 | A1 | 6/2011 | Harris |
| 2011/0208515 | A1 | 8/2011 | Neuhauser et al. |
| 2011/0237971 | A1 | 9/2011 | Pradeep et al. |
| 2011/0248729 | A2 | 10/2011 | Mueller et al. |
| 2011/0270620 | A1 | 11/2011 | Pradeep et al. |
| 2011/0276504 | A1 | 11/2011 | Pradeep et al. |
| 2011/0282231 | A1 | 11/2011 | Pradeep et al. |
| 2011/0282232 | A1 | 11/2011 | Pradeep et al. |
| 2011/0282749 | A1 | 11/2011 | Pradeep et al. |
| 2011/0319975 | A1 | 12/2011 | Ho et al. |
| 2012/0002848 | A1 | 1/2012 | Hill |
| 2012/0036004 | A1 | 2/2012 | Pradeep et al. |
| 2012/0036005 | A1 | 2/2012 | Pradeep et al. |
| 2012/0046993 | A1 | 2/2012 | Hill |
| 2012/0054018 | A1 | 3/2012 | Pradeep et al. |
| 2012/0072289 | A1 | 3/2012 | Pradeep et al. |
| 2012/0083668 | A1 | 4/2012 | Pradeep et al. |
| 2012/0084139 | A1 | 4/2012 | Pradeep et al. |
| 2012/0108995 | A1 | 5/2012 | Pradeep et al. |
| 2012/0114305 | A1 | 5/2012 | Holden |
| 2012/0130800 | A1 | 5/2012 | Pradeep et al. |
| 2012/0239407 | A1 | 9/2012 | Lynch et al. |
| 2012/0245978 | A1 | 9/2012 | Crystal et al. |
| 2012/0284112 | A1 | 11/2012 | Pradeep et al. |
| 2012/0284332 | A1 | 11/2012 | Pradeep et al. |
| 2012/0290409 | A1 | 11/2012 | Pradeep et al. |
| 2013/0022948 | A1 | 1/2013 | Angell et al. |
| 2013/0024272 | A1 | 1/2013 | Pradeep et al. |
| 2013/0046577 | A1 | 2/2013 | Marci et al. |
| 2013/0094722 | A1 | 4/2013 | Hill |
| 2013/0097715 | A1 | 4/2013 | Fourman |
| 2013/0124365 | A1 | 5/2013 | Pradeep |
| 2013/0152506 | A1 | 6/2013 | Pradeep |
| 2013/0166373 | A1 | 7/2013 | Pradeep et al. |
| 2013/0185140 | A1 | 7/2013 | Pradeep et al. |
| 2013/0185141 | A1 | 7/2013 | Pradeep et al. |
| 2013/0185142 | A1 | 7/2013 | Pradeep et al. |
| 2013/0185144 | A1 | 7/2013 | Pradeep et al. |
| 2013/0185145 | A1 | 7/2013 | Pradeep et al. |
| 2013/0268279 | A1 | 10/2013 | Srinivasan et al. |
| 2013/0304540 | A1 | 11/2013 | Pradeep et al. |
| 2013/0332259 | A1 | 12/2013 | Pradeep et al. |
| 2014/0162225 | A1 | 6/2014 | Hill |
| 2014/0244345 | A1 | 8/2014 | Sollis et al. |

FOREIGN PATENT DOCUMENTS

| | | | | |
|---|---|---|---|---|
| GB | 1374658 | | 11/1974 | |
| GB | 2221759 | | 2/1990 | |
| JP | 2001147944 | | 5/2001 | |
| JP | 2005-160805 | | 12/2003 | |
| JP | 2005051654 | | 2/2005 | |
| JP | 2006006355 | | 1/2006 | |
| JP | 2006-305334 | | 3/2006 | |
| JP | 2006227994 | | 8/2006 | |
| KR | 200422399 | | 7/2006 | |
| WO | 95-018565 | | 7/1995 | |
| WO | 1997/017774 | | 5/1997 | |
| WO | 1997/040745 | | 11/1997 | |
| WO | 1997/041673 | | 11/1997 | |
| WO | 02-100241 | | 12/2002 | |
| WO | 02-102238 | | 12/2002 | |
| WO | 2004/049225 | | 6/2004 | |
| WO | 2006-009771 | | 1/2006 | |
| WO | 2008030831 | | 3/2008 | |
| WO | 2008055078 | | 5/2008 | |
| WO | 2008064431 | | 6/2008 | |
| WO | 2008077178 | | 7/2008 | |
| WO | WO2008077178 | * | 7/2008 | ........... A61B 5/0484 |
| WO | 2008/109694 | | 9/2008 | |
| WO | 2008/109699 | | 9/2008 | |
| WO | 2008/121651 | | 10/2008 | |
| WO | 2008/137579 | | 11/2008 | |
| WO | 2008137581 | | 11/2008 | |
| WO | 2008141340 | | 11/2008 | |
| WO | 2008/154410 | | 12/2008 | |
| WO | 2009/018374 | | 2/2009 | |
| WO | 2009/052833 | | 4/2009 | |

OTHER PUBLICATIONS

Examiner's Answer, issued by the United States Patent and Trademark Office in connection with U.S. Appl. No. 13/730,550, dated Jul. 27, 2016, 20 pages.

Advisory Action, issued by the United States Patent and Trademark Office in connection with U.S. Appl. No. 12/234,372, dated Aug. 8, 2016, 3 pages.

Non-Final Office Action, issued by the United States Patent and Trademark Office in connection with U.S. Appl. No. 12/413,297, dated Aug. 16, 2016, 5 pages.

Final Office Action, issued by the United States Patent and Trademark Office in connection with U.S. Appl. No. 12/410,372, dated Aug. 25, 2016, 61 pages.

English Translation of Notification of Provisional Rejection, issued by the Korean Patent Office in connection with Patent Application No. 10-2010-7001406, dated Jul. 27, 2016, 4 pages.

Final Office Action, issued by the United States Patent and Trademark Office in connection with U.S. Appl. No. 12/410,380, dated Mar. 22, 2016, 27 pages.

Final Office Action, issued by the United States Patent and Trademark Office in connection with U.S. Appl. No. 12/608,685, dated Mar. 30, 2016, 23 pages.

Advisory Action, issued by the United States Patent and Trademark Office in connection with U.S. Appl. No. 13/708,525, dated Apr. 6, 2016, 3 pages.

Examiner's Answer, issued by the United States Patent and Trademark Office in connection with U.S. Appl. No. 13/730,564, dated Apr. 8, 2016, 7 pages.

M. Corbetta et al., "Control of Goal-Directed and Stimulus-Driven Attention in the Brain," Nature Reviews Neuroscience, vol. 3, pp. 201-215 (Mar. 2002), 15 pages.

Decision on Appeal, issued by the United States Patent and Trademark Office in connection with U.S. Appl. No. 12/413,297, dated Nov. 27, 2015, 5 pages.

Final Office Action, issued by the United States Patent and Trademark Office in connection with U.S. Appl. No. 13/965,805, dated Apr. 21, 2016, 33 pages.

Final Office Action, issued by the United States Patent and Trademark Office in connection with U.S. Appl. No. 12/234,372, dated May 12, 2016, 61 pages.

Non-Final Office Action, issued by the United States Patent and Trademark Office in connection with U.S. Appl. No. 12/884,034, dated May 20, 2016, 69 pages.

Non-Final Office Action, issued by the United States Patent and Trademark Office in connection with U.S. Appl. No. 13/945,357, dated May 20, 2016, 22 pages.

Becker, "A Study of Web Usability for Older Adults Seeking Online Health Resources," ACM Transactions on Computer-Human Interaction, vol. 11, No. 4, pp. 387-406 (Dec. 2004), 20 pages.

Knutson et al., "Neural Predictors of Purchases," Neuron vol. 53 (Jan. 4, 2007), pp. 147-156, 10 pages.

Schaefer et al., "Neural Correlates of Culturally Familiar Brands of Car Manufacturers," Neuroimiage, vol. 31 (2006), pp. 861-865, 5 pages.

Aharon et al., "Beautiful Faces Have Variable Reward Value: fMRI and Behavorial Evidence," Neuron, vol. 32 (2001), pp. 537-551, 15 pages.

(56) References Cited

OTHER PUBLICATIONS

Non-Final Office Action, issued by the United States Patent and Trademark Office in connection with U.S. Appl. No. 14/177,698, dated Oct. 24, 2014, 13 pages.
English Translation of Notification of Provisional Rejection, issued by the Korean Patent Office in connection with Patent Application No. 10-2010-7001406, dated Oct. 21, 2014, 1 page.
Final Office Action, issued by the United States Patent and Trademark Office in connection with U.S. Appl. No. 13/708,525, dated Feb. 3, 2016, 23 pages.
Examiner's Answer, issued by the United States Patent and Trademark Office in connection with U.S. Appl. No. 13/730,511, dated Feb. 18, 2016, 5 pages.
Non-Final Office Action, issued by the United States Patent and Trademark Office in connection with U.S. Appl. No. 12/410,372, dated Feb. 23, 2016, 24 pages.
Decision on Appeal, issued by the United States Patent and Trademark Office in connection with U.S. Appl. No. 12/410,380, dated Mar. 30, 2015, 6 pages.
Decision on Appeal, issued by the United States Patent and Trademark Office in connection with U.S. Appl. No. 12/234,372, dated Jun. 15, 2015, 5 pages.
Non-Final Office Action, issued by the United States Patent and Trademark Office in connection with U.S. Appl. No. 12/234,372, dated Sep. 23, 2015, 16 pages.
Decision on Appeal, issued by the United States Patent and Trademark Office in connection with U.S. Appl. No. 12/410,372, dated Sep. 22, 2015, 6 pages.
English Translation of Office Action, issued by the Japanese Patent Office in connection with Patent Application No. 2010-501190, dated Oct. 2, 2012, 10 pages.
English Translation of Notification of Provisional Rejection, issued by the Korean Patent Office in connection with Patent Application No. 10-2010-7001406, dated Jan. 26, 2016, 1 page.
English Translation of Notification to Grant Patent Right for Invention, issued by the State Intellectual Property Office of P.R. China in connection with Patent Application No. 200880017883.X, dated Feb. 3, 2016, 2 pages.
Landau et al., "Different Effects of Voluntary and Involunatry Attention on EEG Activity in the Gamma Band," J ofNeuroscience 27(44), Oct. 31, 2007, pp. 11986-11990, 5 pages.
Final Office Action, issued by the United States Patent and Trademark Office in connection with U.S. Appl. No. 13/708,344, dated Nov. 20, 2015, 18 pages.
Examiner's Answer, issued by the United States Patent and Trademark Office in connection with U.S. Appl. No. 13/730,541, dated Dec. 18, 2015, 7 pages.
Non-Final Office Action, issued by the United States Patent and Trademark Office in connection with U.S. Appl. No. 12/608,685, dated Dec. 17, 2015, 16 pages.
Notice of Allowance, issued by the United States Patent and Trademark Office in connection with U.S. Appl. No. 14/177,698, dated Jan. 14, 2016, 17 pages.
Translation of Reexamination Decision, issued by the Chinese Patent Office in connection with Patent Application No. 200880017883.X, dated Nov. 13, 2015, 1 page.
Extended European Search Report, issued by the European Patent Office in connection with European Application No. 08747389.8, dated Sep. 25, 2015, 6 pages.
Kamba, "The Krakatoa Chronicl—An Interactive, Personalized Newspaper on the Web," available at http://www.w3.org/Conferences/WWW4/Papers/93/ (last accessed Nov. 2, 2015), 15 pages.
Ehrenberg et al., "Understanding Brand Performance Measures: Using Dirichlet Benchmarks," 2004, Journal of Business Research, vol. 57, pp. 1307-1325, 19 pages.
Leeflang et al., "Building Models for Marketing Decisions," 2000, Springer Science + Business Media, pp. 192-235, 482-521, 86 pages.
Bhattacharya, "Is your brand's loyalty too much, too little, or just right?: Explaining deviations in loyalty from the Dirichlet norm," 1997, International Journal of Research in Marketing, vol. 14, pp. 421-435, 15 pages.
Cohen, "Differentiated product demand analysis with a structured covariance probit: A Bayesian econometric approach," 2009, PhD dissertation, University of Connecticut, pp. 1-184, 197 pages.
Nikolaeva et al., "The Moderating Role of Consumer and Product Characteristics on the Value of Customized On-Line Recommendations," 2006, International Journal of Electronic Commerce, vol. 11, No. 2, pp. 101-123,24 pages.
Ehrenberg, "New Brands and the Existing Market," 1991, International Journal of Market Research, vol. 33, No. 4, 10 pages.
Foxall, "The Substitutability of Brands," 1999, Managerial and Decision Economics, vol. 20, pp. 241-257, 17 pages.
Pammer, "Forecasting the Penetration of a New Product—A Bayesian Approach," 2000, Journal of Business and Economic Statistics, vol. 18, No. 4, pp. 428-435, 8 pages.
Rungie et al., "Calculation of Theoretical Brand Performance Measures from the Parameters of the Dirichlet Model," 2004, Marketing Bulletin, Massey University, 15, Technical Note 2, pp. 1-19, 20 pages.
Uncles et al., "Patterns of Buyer Behavior: Regularities, Models, and Extensions," 1995, Marketing Science, vol. 14, No. 3, pp. G71-G78, 9 pages.
Boltz, "The cognitive processing of film and musical soundtracks," Haverford College, Haverford, Pennsylvania, 2004, 32 (7), 1194-1205, 12 pages.
Christie et al., "Autonomic specificity of discrete emotion and dimensions of affective space: a multivariate approach," International Journal of Psychophysiology, 51 (2004) 143-153, 11 pages.
Coombes et al., "Emotion and movement: Activation of defensive circuitry alters the magnitude of a sustained muscle contraction," University of Florida, Neuroscience Letters 396 (2006) 192-196, 5 pages.
CRYer et al., "Pull the Plug on Stress," Harvard Business Review, Jul. 2003, 8 pages.
Demaree et al., "Predicting facial valence to negative stimuli from resting RSA: Not a function of active emotion regulation," Cognition and Emotion, vol. 20, Issue 2, 2006, pp. 161-176, published on Sep. 9, 2010, http://www.tandfonline.com/doi/abs/10.1080/02699930500260427, 6 pages.
Ekman et al., "Autonomic Nervous System Activity Distinguishes among Emotions," Science, New Series, vol. 221, No. 4616. (Sep. 16, 1983), pp. 1208-1210, http://links.jstor.org/sici?sici=0036-8075%2819830916%293%3A221%3A4616%3C1208%3AANSADA%3E2.0.C0%3B2-R, 5 pages.
Elton, "Measuring emotion at the symphony," The Boston Globe, Apr. 5, 2006, http://www.psych.mcgill.ca/labs/levitinlmedia/measuring emotion boston.html, 3 pages.
Goldberg, "Getting wired could help predict emotions," The Boston Globe, Jun. 13, 2005, http://www.boston.com/yourlife/health!mental/articles/2005/06/13/getting_ wired_ could_ help predict_emotions/?page=full, 4 pages.
Gomez et al., "Respiratory Responses Associated with Affective Processing of Film Stimuli," Biological Psychology, vol. 68, Issue 3, Mar. 2005, pp. 223-235, 2 pages.
Hall, "Is cognitive processing the right dimension," World Advertising Research Center, Jan. 2003, 3 pages.
Hall, "On Measuring the Power of Communications," Journal of Advertising Research, 44, pp. 1-11, doi: 10.1017 /S0021849904040139, (2004), 1 page.
Hall, "Research and strategy: a fall from grace," ADMAP, Issue 443, pp. 18-20,2003, 1 page.
Hubert et al., "Autonomic, neuroendocrine, and subjective responses to emotion-inducing film stimuli," Int. J Psychophysiol, Aug. 1991, 2 pages.
Levenson et al., "Emotion and Autonomic Nervous System Activity in the Minangkabau of West Sumatra," Department of Psychology, University of California, Berkeley, Journal of Personality and Social Psychology, 1992, 2 pages.
Marci et al., "The effect of emotional distance on psychophysiologic concordance and perceived empathy between patient and inter-

(56) References Cited

OTHER PUBLICATIONS viewer," Applied Psychophysiology and Biofeedback, Jun. 2006, vol. 31, Issue 2, 31:115-129, 8 pages.
McCraty et al., "Analysis of twenty-four hour heart rate variability in patients with panic disorder," Biological Psychology, vol. 56, Issue 2, Jun. 2001, pp. 131-150, 1 page.
McCraty et al., "Electrophysiological Evidence ofIntuition: Part 1. The Surprising Role of the Heart" The Journal of Alternative and Complementary Medicine, vol. 10, No. 1, 2004, pp. 133-143, 12 pages.
McCraty et al., "Electrophysiological Evidence ofIntuition: Part 2. A System-Wide Process?," The Journal of Alternative and Complementary Medicine, vol. 10, No. 2, 2004, pp. 325-336, 12 pages.
McCraty et al., "The Effects of Different Types of Music on Mood, Tension, and Mental Clarity," Original Research, Alternative Therapies, Jan. 1998, vol. 4., No. 1, pp. 75-84, 10 pages.
McCraty et al., "The Effects of Emotions on Short-Term Power Spectrum Analysis of Heart Rate Variability," American Journal of Cardiology, vol. 76, No. 14, Nov. 15, 1995, pp. 1089-1093, 6 pages.
McCraty et al., "The Impact of a New Emotional Self-Management Program on Stress, Emotions, Heart Rate Variability, DHEA and Cortisol," Integrative Physiological and Behavioral Science, Apr.-Jun. 1998, vol. 33, No. 2, 151-170, 20 pages.
McCraty et al., "The Impact of an Emotional Self-Management Skills Course on Psychosocial Functioning and Autonomic Recovery to Stress in Middle School Children," Integrative Physiological and Behavioral Science, Oct.-Dec. 1999, vol. 34, No. 4, 246-268, 23 pages.
Melillo, "Inside the Consumer Mind; What Neuroscience Can Tell Us About Marketing," Adweek, Public Citizen's Commercial Alert, Jan. 16, 2006, http://www.adweek.com/news/advertising/inside-consumer-mind-83549, 8 pages.
Miller et al., "Influence of Specific Emotional States on Autonomic Reactivity and Pulmonary Function in Asthmatic Children," Journal of the American Academy of Child & Adolescent Psychiatry, vol. 36, Issue 5, May 1997, pp. 669-677, 3 pages.
Murphy et al., "The Heart Reinnervates After Transplantation," Official Journal of the Society of Thoracic Surgeons and the Southern Thoracic Surgical Association, Jun. 2000, vol. 69, Issue 6, pp. 1769-1781, 13 pages.
Rosenberg, "Emotional R.O.I.," The Hub, May/Jun. 2006, pp. 24-25, 2 pages.
Tiller et al., "Cardiac Coherence: A New, Noninvasive Measure of Autonomic Nervous System Order," Alternative Therapies, Jan. 1996, vol. 2, No. 1, 14 pages.
Umetani et al. "Twenty-Four Hour Time Domain Heart Rate Variability and Heart Rate: Relations to Age and Gender Over Nine Decades," J Am Coll Cardiol, Mar. 1, 1998, pp. 593-601, 9 pages.
Von Leupoldt et al., "Emotions in a Body Plethysmograph," Journal of Psychophysiology (2004), 18, pp. 170-176, 1 page.
Kallman et al., "Effect of Blank Time on Picture Recognition," The American Journal of Psychology, vol. 97, No. 3 (Autumn, 1984), pp. 399-406, 4 pages.
Larose, Data Mining Methods and Models, Department of Mathematical Sciences, Central Connecticut State University, www.dbeBooks.com—An Ebook Library,published by John Wiley & Sons, Inc., 2006, 340 pages (Book).
Han et al., Data Mining: Concepts and Techniques, 2na Edition, Elsevier, 2006, 772 pages (Book).
Liu et al., Web Data Mining: Exploring Hyperlinks, Contents, and Usage Data, Springer Science & Business Media, 2007, 532 pages, (Book).
Berry et al., Data Mining Techniques: For Marketing, Sales, and Customer Support, Wiley Publishing Inc., Jun. 1997, 464 pages (Book).
Horovitz, "Watching Ads Is Real Science Research Companies Monitor Physiological Reactions to Commercials to Determine Their Effectiveness," Los Angeles Times, Sep. 1, 1991, 3 pages.
Sung et al., "Wearable feedback systems for rehabilitation," Journal of NeuroEngineering and Rehabilitation, 2005, 12 pages.
Jaffe, Casting for Big Ideas, Adweek Magazine Series, Book 8, 2003, 256 pages (Book).
Hall "A New Model for Measuring Advertising Effectiveness," J. Advertising Research, vol. 42(2), Mar./Apr. 2002, 1 page.
Hall "Advertising as a Factor of Production," ADMAP, 2003, pp. 20-23, 1 page.
Ranii, "Adding Science to Gut Check," The News & Observer, D3 (Apr. 6, 2005), 1 page.
McCraty et al., "Impact of a Workplace Stress Reduction Program on Blood Pressure and Emotional Health in Hypertensive Employees", Journal of Alternative and Complementary Medicine, vol. 9, No. 3, 2003, pp. 355-369, 15 pages.
Schaefer et al., "Neural Correlates of Culturally Familiar Brands of Car Manufacturers," Neuroimage, vol. 31, 2006, pp. 861-865, 5 pages.
Landau et al. "Different Effects of Voluntary and Involuntary Attention on EEG Activity in the Gamma Band," The Journal of Neuroscience, Oct. 31, 2007, 27(44):11986-11990, 5 pages.
Non-Final Office Action, issued by the United States Patent and Trademark Office in connection with U.S. Appl. No. 13/730,550, dated Feb. 20, 2015, 5 pages.
Final Office Action, issued by the United States Patent and Trademark Office in connection with U.S. Appl. No. 12/608,660, dated Feb. 20, 2015, 18 pages.
Final Office Action, issued by the United States Patent and Trademark Office in connection with U.S. Appl. No. 13/965,805, dated Mar. 6, 2015, 18 pages.
Non-Final Office Action, issued by the United States Patent and Trademark Office in connection with U.S. Appl. No. 13/708,344, dated Apr. 9, 2015, 12 pages.
Final Office Action, issued by the United States Patent and Trademark Office in connection with U.S. Appl. No. 13/730,541, dated Feb. 12, 2015, 6 pages.
Final Office Action, issued by the United States Patent and Trademark Office in connection with U.S. Appl. No. 14/177,698, dated Apr. 24, 2015, 13 pages.
Final Office Action, issued by the United States Patent and Trademark Office in connection with U.S. Appl. No. 12/608,685, dated May 5, 2015, 7 pages.
Final Office Action, issued by the United States Patent and Trademark Office in connection with U.S. Appl. No. 13/730,511, dated May 6, 2015, 5 pages.
Final Office Action, issued by the United States Patent and Trademark Office in connection with U.S. Appl. No. 13/105,774, dated May 14, 2015, 15 pages.
Final Office Action, issued by the United States Patent and Trademark Office in connection with U.S. Appl. No. 12/884,034, dated May 14, 2015, 22 pages.
Final Office Action, issued by the United States Patent and Trademark Office in connection with U.S. Appl. No. 13/730,564, dated May 22, 2015, 6 pages.
Final Office Action, issued by the United States Patent and Trademark Office in connection with U.S. Appl. No. 13/249,512, dated Jun. 30, 2015, 36 pages.
English Translation of Office Action, issued by the Israeli Patent Office in connection with Patent Application No. 201187, dated Jun. 22, 2015, 4 pages.
Notification of Provisional Rejection, issued by the Korean Patent Office in connection with Patent Application No. 10-2010-7001406, dated Jun. 24, 2015 (with partial translation), 9 pages.
McClure et al., "Neural Correlates of Behavioral Preference for Culturally Familiar Drinks," Neuron (Oct. 14, 2004), 379-387, 9 pages.
Examiner's Answer, issued by the United States Patent and Trademark Office in connection with U.S. Appl. No. 12/113,870, dated Jul. 30, 2015, 14 pages.
Examiner's Answer, issued by the United States Patent and Trademark Office in connection with U.S. Appl. No. 12/122,253, dated Aug. 4, 2015, 30 pages.
Non-Final Office Action, issued by the United States Patent and Trademark Office in connection with U.S. Appl. No. 14/177,698, dated Aug. 19, 2015, 12 pages.

(56) References Cited

OTHER PUBLICATIONS

Examiner's Answer, issued by the United States Patent and Trademark Office in connection with U.S. Appl. No. 12/546,586, dated Sep. 11, 2015, 7 pages.
Final Office Action, issued by the United States Patent and Trademark Office in connection with U.S. Appl. No. 13/730,550, dated Sep. 2, 2015, 5 pages.
Non-Final Office Action, issued by the United States Patent and Trademark Office in connection with U.S. Appl. No. 12/410,380, dated Sep. 10, 2015, 15 pages.
Advisory Action, issued by the United States Patent and Trademark Office in connection with U.S. Appl. No. 12/884,034, dated Sep. 16, 2015, 3 pages.
Non-Final Office Action, issued by the United States Patent and Trademark Office in connection with U.S. Appl. No. 13/708,525, dated Sep. 30, 2015, 12 pages.
Non-Final Office Action, issued by the United States Patent and Trademark Office in connection with U.S. Appl. No. 13/965,805, dated Sep. 30, 2015, 6 pages.
Opitz, S. "Neuromarketing: An Introduction" Power Point Presentation (2008), available at http://www.powershow.com/view/94a7b-YzlmN/Neuromarketing_powerpoint_ppt_presentation (last accessed Oct. 14, 2015), 20 pages.
Non-Final Office Action, issued by the United States Patent and Trademark Office in connection with U.S. Appl. No. 13/730,541, dated Jul. 23, 2014, 13 pages.
Non-Final Office Action, issued by the United States Patent and Trademark Office in connection with U.S. Appl. No. 13/965,805, dated Aug. 6, 2014, 18 pages.
Non-Final Office Action, issued by the United States Patent and Trademark Office in connection with U.S. Appl. No. 13/730,511, dated Aug. 13, 2014, 4 pages.
Non-Final Office Action, issued by the United States Patent and Trademark Office in connection with U.S. Appl. No. 13/730,550, dated Aug. 14, 2014, 4 pages.
Non-Final Office Action, issued by the United States Patent and Trademark Office in connection with U.S. Appl. No. 13/730,564, dated Aug. 15, 2014, 15 pages.
Non-Final Office Action, issued by the United States Patent and Trademark Office in connection with U.S. Appl. No. 12/884,034, dated Aug. 21, 2014, 20 pages.
Non-Final Office Action, issued by the United States Patent and Trademark Office in connection with U.S. Appl. No. 12/608,685, dated Sep. 4, 2014, 16 pages.
Non-Final Office Action, issued by the United States Patent and Trademark Office in connection with U.S. Appl. No. 13/105,774, dated Sep. 18, 2014, 14 pages.
Final Office Action, issued by the United States Patent and Trademark Office in connection with U.S. Appl. No. 12/546,586, dated Sep. 29, 2014, 21 pages.
Decision to Grant Patent, issued by the Korean Patent Office in connection with Patent Application No. 10-2009-7022551, dated Aug. 13, 2014, 3 pages.
Ekman et al., Measuring Facial Movement, Environmental Psychology and Nonverbal Behavior, 1 (1) (Fall 1976), pp. 56-75, 20 pages.
Ekman et al., *Facial Action Coding System: A Technique for Measurement of Facial Movement*, Consulting Psychologists Press, Palo Alto, Calif (1978) (Book).
Ekman et al., *Unmasking the Face—A Guide to Recognizing Emotions from Facial Clues*, Prentice-Hall, Inc., Englewood Cliffs, N.J. (1979), 212 pages.
Ekman et al., Facial Signs of Emotional Experience, J. Personality & Social Psychology, 39(6) (Dec. 1980), pp. 1125-1134, 10 pages.
Izard, *The Maximally Discriminative Facial Movement Coding System*, (Rev. ed.), Instructional Resources Center, University of Delaware, Newark, Del. (1983) (Book).
Izard et al., *A System for Identifying Affect Expressions by Holistic Judgments* (*AFFEX*), Instructional Resources Center, University of Delaware, Newark, Del. (1983) (Book).
Jia, X et al., Extending the Feature Set for Automatic Face Recognition, International Conference on Image Processing and Its Applications (Apr. 7-9, 1992), 6 pages.
Lisetti et al., "Using Noninvasive Wearable Computers to Recognize Human Emotions from Physiological Signals," EURASIP J. Applied Signal Processing, 11 (Sep. 2004), pp. 1672-1687, 16 pages.
Jaimes et al., Multimodal Human-Computer Interaction: A Survey, Computer Vision and Image Understanding 108 (Oct.-Nov. 2007), pp. 116-134, 19 pages.
Notice of Allowance, issued by the United States Patent and Trademark Office in connection with U.S. Appl. No. 13/730,550, dated May 27, 2014, 8 pages.
Notice of Allowance, issued by the United States Patent and Trademark Office in connection with U.S. Appl. No. 13/730,511, dated May 29, 2014, 8 pages.
Office Action, issued by the United States Patent and Trademark Office in connection with U.S. Appl. No. 12/122,253, dated Jun. 5, 2014, 25 pages.
Final Office Action, issued by the United States Patent and Trademark Office in connection with U.S. Appl. No. 12/113,870, dated Jul. 1, 2014, 16 pages.
Decision to Grant Patent, issued by the Japanese Patent Office in connection with Patent Application No. 2010-523112, on Apr. 8, 2014, 4 pages.
English Translation of Office Action, issued by the Israeli Patent Office in connection with Patent Application No. 201187, dated Apr. 23, 2014, 2 pages.
Darrow, "Psychological and psychophysiological significance of the electroencephalogram,"Psychological Review (May 1947) 157-168, 12 pages.
Stamm, "On the Relationship between Reaction Time to Light and Latency of Blocking the Alpha Rhythm," Electroencephalography and Clinical Neurophysiology (Feb. 1952), 61-68, 8 pages.
Mizuki et al., "Periodic Appearance of the Theta Rhythm in the Frontal Midline Area During Performance of a Mental Task," Electroencephalography and Clinical Neurophysiology (Aug. 1980), 345-351, 7 pages.
Office Action, issued by the United States Patent and Trademark Office in connection with U.S. Appl. No. 13/730,511, dated Jan. 30, 2014, 6 pages.
Office Action, issued by the United States Patent and Trademark Office in connection with U.S. Appl. No. 13/730,550, dated Jan. 31, 2014, 5 pages.
Office Action, issued by the United States Patent and Trademark Office in connection with U.S. Appl. No. 13/965,805, dated Feb. 3, 2014, 15 pages.
Notice of Allowance, issued by the United States Patent and Trademark Office in connection with U.S. Appl. No. 13/444,149, dated Feb. 3, 2014, 5 pages.
Office Action, issued by the United States Patent and Trademark Office in connection with U.S. Appl. No. 12/113,870, dated Feb. 4, 2014, 12 pages.
Office Action, issued by the United States Patent and Trademark Office in connection with U.S. Appl. No. 12/546,586, dated Feb. 6, 2014, 17 pages.
Office Action, issued by the United States Patent and Trademark Office in connection with U.S. Appl. No. 13/730,564, dated Feb. 10, 2014, 14 pages.
Office Action, issued by the United States Patent and Trademark Office in connection with U.S. Appl. No. 112/884,034, dated Feb. 10, 2014, 18 pages.
Axis Communications, "Improve your merchandising effectiveness. Get the full picture with network video" (2008), available at :http://www.axis.com/files/user_scenario slap _ret_merchandising_31107 en 0803 lo.pdf, 2 pages.
Brown, M. "Should My Advertising Stimulate an Emotional Response?" (2009) available at http://www.wpp.com/~/media/sharedwpp/readingroom/marketing/millward brown_emotional_response.pdf, 6 pages.
Mehta, A. et al., "Reconsidering Recall and Emotion in Advertising", Journal of Advertising Research, (Mar. 2006), 49-56, 8 pages.

(56) References Cited

OTHER PUBLICATIONS

Cheung et al., "Mining Customer Product Ratings for Personalized Marketing," Decision Support Systems 35 (2003) 231-243, 13 pages.
Notice of Allowance, issued by the United States Patent and Trademark Office in connection with U.S. Appl. No. 12/199,557, dated Jan. 29, 2013, 17 pages.
Notice of Allowance, issued by the United States Patent and Trademark Office in connection with U.S. Appl. No. 12/853,197, dated Jan. 29, 2013, 11 pages.
Notice of Allowance, issued by the United States Patent and Trademark Office in connection with U.S. Appl. No. 12/056,190, dated Jan. 31, 2013, 5 pages.
Notice of Allowance, issued by the United States Patent and Trademark Office in connection with U.S. Appl. No. 12/113,863, dated Jan. 31, 2013, 5 pages.
Notice of Allowance, issued by the United States Patent and Trademark Office in connection with U.S. Appl. No. 12/135,074, dated Jan. 31, 2013, 10 pages.
Notice of Allowance, issued by the United States Patent and Trademark Office in connection with U.S. Appl. No. 12/199,583, dated Feb. 1, 2013, 11 pages.
Notice of Allowance, issued by the United States Patent and Trademark Office in connection with U.S. Appl. No. 12/200,813, dated Feb. 1, 2013, 5 pages.
Notice of Allowance, issued by the United States Patent and Trademark Office in connection with U.S. Appl. No. 12/056,211, dated Feb. 4, 2013, 5 pages.
Notice of Allowance, issued by the United States Patent and Trademark Office in connection with U.S. Appl. No. 12/122,262, dated Feb. 5, 2013, 15 pages.
Notice of Allowance, issued by the United States Patent and Trademark Office in connection with U.S. Appl. No. 12/868,531, dated Feb. 5, 2013, 8 pages.
Notice of Allowance, issued by the United States Patent and Trademark Office in connection with U.S. Appl. No. 12/853,213, dated Feb. 5, 2013, 10 pages.
Notice of Allowance, issued by the United States Patent and Trademark Office in connection with U.S. Appl. No. 12/056,190, dated Feb. 14, 2013, 5 pages.
Notice of Allowance, issued by the United States Patent and Trademark Office in connection with U.S. Appl. No. 12/234,388, dated Feb. 15, 2013, 9 pages.
Notice of Allowance, issued by the United States Patent and Trademark Office in connection with U.S. Appl. No. 12/182,874, dated Apr. 16, 2013, 10 pages.
Notice of Allowance, issued by the United States Patent and Trademark Office in connection with U.S. Appl. No. 12/182,874, dated Apr. 22, 2013, 11 pages.
Notification to Grant Patent Right for Invention, issued by the State Intellectual Property Office of P.R. China in connection with Patent Application No. 200880104982.1, dated Jan. 14, 2013, 4 pages.
Extended European Search Report, issued by the European Patent Office in connection with European Application No. 08770372.4-1265/2152155, dated Feb. 6, 2013, 7 pages.
English Translation of Third Office Action, issued by the State Intellectual Property Office of P.R. China in connection with Patent Application No. 200880017883.X, dated Mar. 18, 2013, 8 pages.
Notification to Grant Patent Right for Invention, issued by the State Intellectual Property Office of P.R. China in connection with Patent Application No. 200880101500.7, dated Apr. 3, 2013, 2 pages.
Non-Final Office Action, issued by the United States Patent and Trademark Office in connection with U.S. Appl. No. 12/546,586, dated Apr. 25, 2013, 34 pages.
Non-Final Office Action, issued by the United States Patent and Trademark Office in connection with U.S. Appl. No. 13/444,149, dated May 2, 2013, 27 pages.
Notice of Allowance, issued by the United States Patent and Trademark Office in connection with U.S. Appl. No. 12/056,190, dated May 8, 2013, 4 pages.
Notice of Allowance, issued by the United States Patent and Trademark Office in connection with U.S. Appl. No. 12/056,211, dated May 8, 2013, 5 pages.
Notice of Allowance, issued by the United States Patent and Trademark Office in connection with U.S. Appl. No. 12/135,074, dated May 8, 2013, 5 pages.
Notice of Allowance, issued by the United States Patent and Trademark Office in connection with U.S. Appl. No. 12/199,596, dated May 8, 2013, 7 pages.
Notice of Allowance, issued by the United States Patent and Trademark Office in connection with U.S. Appl. No. 13/569,711, dated May 14, 2013, 6 pages.
Notice of Allowance, issued by the United States Patent and Trademark Office in connection with U.S. Appl. No. 12/182,874, dated May 17, 2013, 6 pages.
Final Office Action, issued by the United States Patent and Trademark Office in connection with U.S. Appl. No. 12/778,828, dated May 23, 2013, 25 pages.
Office Communication to Applicant, issued by the United States Patent and Trademark Office in connection with U.S. Appl. No. 12/234,388, dated May 24, 2013, 2 pages.
Non-Final Office Action, issued by the United States Patent and Trademark Office in connection with U.S. Appl. No. 12/884,034, dated May 28, 2013, 12 pages.
Notice of Allowance, issued by the United States Patent and Trademark Office in connection with U.S. Appl. No. 12/135,074, dated May 31, 2013, 5 pages.
Notice of Allowance, issued by the United States Patent and Trademark Office in connection with U.S. Appl. No. 12/056,211, dated Jun. 3, 2013, 5 pages.
Notice of Allowance, issued by the United States Patent and Trademark Office in connection with U.S. Appl. No. 12/199,596, dated Jun. 3, 2013, 5 pages.
Notice of Allowance, issued by the United States Patent and Trademark Office in connection with U.S. Appl. No. 12/199,596, dated Jun. 11, 2013, 7 pages.
Notice of Allowance, issued by the United States Patent and Trademark Office in connection with U.S. Appl. No. 12/545,455, dated Jun. 11, 2013, 9 pages.
Notice of Allowance, issued by the United States Patent and Trademark Office in connection with U.S. Appl. No. 12/056,190, dated Jun. 13, 2013, 5 pages.
Office Communication to Applicant, issued by the United States Patent and Trademark Office in connection with U.S. Appl. No. 12/234,388, dated Jun. 13, 2013, 2 pages.
Notice of Allowance, issued by the United States Patent and Trademark Office in connection with U.S. Appl. No. 12/135,074, dated Jun. 21, 2013, 5 pages.
Non-Final Office Action, issued by the United States Patent and Trademark Office in connection with U.S. Appl. No. 13/105,774, dated Jun. 26, 2013, 10 pages.
English Translation of Office Action, issued by the Israeli Patent Office in connection with Patent Application No. 203176, dated Apr. 23, 2013, 1 page.
English Translation of Notice Prior to Allowance, issued by the Israeli Patent Office in connection with Patent Application No. 203176, dated Jun. 30, 2013, 1 page.
Merriam-Webster Online Dictionary, Definition for "Resonance," available at http://www.merriamwebster.com/dictionary/resonance, 4 pages.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Notice of Allowance, issued by the United States Patent and Trademark Office in connection with U.S. Appl. No. 12/182,874, dated Jul. 29, 2013, 6 pages.
Office Action, issued by the United States Patent and Trademark Office in connection with U.S. Appl. No. 12/546,586, dated Sep. 12, 2013, 13 pages.

(56) References Cited

OTHER PUBLICATIONS

Notice of Allowance, issued by the United States Patent and Trademark Office in connection with U.S. Appl. No. 12/199,596, dated Sep. 13, 2013, 7 pages.
Office Action, issued by the United States Patent and Trademark Office in connection with U.S. Appl. No. 12/113,870, dated Sep. 17, 2013, 11 pages.
Notice of Allowance, issued by the United States Patent and Trademark Office in connection with U.S. Appl. No. 12/778,828, dated Oct. 8, 2013, 11 pages.
English Translation of Office Action, issued by the Japanese Patent Office in connection with Patent Application No. 2010-523112, dated Jul. 30, 2013, 2 pages.
Decision to Grant Patent, issued by the Japanese Patent Office in connection with Patent Application No. 2010-506646, dated Aug. 6, 2013, 4 pages.
English Translation of Decision on Rejection, issued by the Chinese Patent Office in connection with Patent Application No. 200880017883.X, dated Aug. 5, 2013, 13 pages.
Final Office Action, issued by the United States Patent and Trademark Office in connection with U.S. Appl. No. 12/608,660, dated Jul. 10, 2012, 14 pages.
Notice of Allowance, issued by the United States Patent and Trademark Office in connection with U.S. Appl. No. 12/357,302, dated May 7, 2012, 11 pages.
Notice of Allowance, issued by the United States Patent and Trademark Office in connection with U.S. Appl. No. 12/608,696, dated May 15, 2012, 6 pages.
Notice of Allowance, issued by the United States Patent and Trademark Office in connection with U.S. Appl. No. 12/868,531, dated May 8, 2012, 11 pages.
Examiner's Answer, issued by the United States Patent and Trademark Office in connection with U.S. Appl. No. 12/234,372, dated May 23, 2012, 11 pages.
Examiner's Answer, issued by the United States Patent and Trademark Office in connection with U.S. Appl. No. 12/410,380, dated Jun. 8, 2012, 12 pages.
Restriction Requirement, issued by the United States Patent and Trademark Office in connection with U.S. Appl. No. 12/545,455, dated Jun. 13, 2012, 5 pages.
Office Action, issued by the United States Patent and Trademark Office in connection with U.S. Appl. No. 12/056,225, dated Jun. 15, 2012, 9 pages.
Office Action, issued by the United States Patent and Trademark Office in connection with U.S. Appl. No. 12/544,934, dated Jun. 18, 2012, 11 pages.
Final Office Action, issued by the United States Patent and Trademark Office in connection with U.S. Appl. No. 12/608,685, dated Jul. 30, 2012, 15 pages.
Examiner's Answer, issued by the United States Patent and Trademark Office in connection with U.S. Appl. No. 12/410,372, dated Aug. 3, 2012, 8 pages.
Advisory Action, issued by the United States Patent and Trademark Office in connection with U.S. Appl. No. 12/234,388, dated Aug. 28, 2012, 3 pages.
Office Action, issued by the United States Patent and Trademark Office in connection with U.S. Appl. No. 12/545,455, dated Aug. 29, 2012, 11 pages.
Office Action, issued by the United States Patent and Trademark Office in connection with U.S. Appl. No. 12/778,810, dated Aug. 31, 2012, 12 pages.
Office Action, issued by the United States Patent and Trademark Office in connection with U.S. Appl. No. 12/778,828, dated Aug. 30, 2012, 9 pages.
Notice of Allowance, issued by the United States Patent and Trademark Office in connection with U.S. Appl. No. 12/853,213, dated Sep. 7, 2012, 9 pages.
Final Office Action, issued by the United States Patent and Trademark Office in connection with U.S. Appl. No. 12/122,253, dated Sep. 17, 2012, 17 pages.
Notice of Allowance, issued by the United States Patent and Trademark Office in connection with U.S. Appl. No. 12/056,190, dated Sep. 17, 2012, 11 pages.
Notice of Allowance, issued by the United States Patent and Trademark Office in connection with U.S. Appl. No. 12/122,262, dated Sep. 17, 2012, 11 pages.
Examiner's Answer, issued by the United States Patent and Trademark Office in connection with U.S. Appl. No. 12/413,297, dated Sep. 18, 2012, 18 pages.
Final Office Action, issued by the United States Patent and Trademark Office in connection with U.S. Appl. No. 12/546,586, dated Sep. 18, 2012, 17 pages.
Notice of Allowance, issued by the United States Patent and Trademark Office in connection with U.S. Appl. No. 12/056,211, dated Sep. 19, 2012, 10 pages.
Notice of Allowance, issued by the United States Patent and Trademark Office in connection with U.S. Appl. No. 12/135,074, dated Sep. 19, 2012, 10 pages.
Notice of Allowance, issued by the United States Patent and Trademark Office in connection with U.S. Appl. No. 12/200,813, dated Sep. 20, 2012, 11 pages.
Notice of Allowance, issued by the United States Patent and Trademark Office in connection with U.S. Appl. No. 12/199,583, dated Sep. 26, 2012, 14 pages.
Notice of Allowance, issued by the United States Patent and Trademark Office in connection with U.S. Appl. No. 12/199,596, dated Sep. 27, 2012, 14 pages.
Notice of Allowance, issued by the United States Patent and Trademark Office in connection with U.S. Appl. No. 12/199,557, dated Sep. 28, 2012, 12 pages.
Notice of Allowance, issued by the United States Patent and Trademark Office in connection with U.S. Appl. No. 12/113,863, dated Oct. 1, 2012, 12 pages.
Office Action, issued by the United States Patent and Trademark Office in connection with U.S. Appl. No. 13/444,149, dated Oct. 4, 2012, 9 pages.
Final Office Action, issued by the United States Patent and Trademark Office in connection with U.S. Appl. No. 12/182,851, dated Oct. 4, 2012, 14 pages.
Office Action, issued by the United States Patent and Trademark Office in connection with U.S. Appl. No. 12/234,388, dated Oct. 5, 2012, 6 pages.
Notice of Allowance, issued by the United States Patent and Trademark Office in connection with U.S. Appl. No. 12/853,197, dated Oct. 16, 2012, 5 pages.
Notice of Allowance, issued by the United States Patent and Trademark Office in connection with U.S. Appl. No. 12/868,531, dated Oct. 22, 2012, 5 pages.
Notice of Allowance, issued by the United States Patent and Trademark Office in connection with U.S. Appl. No. 12/200,813, dated Oct. 30, 2012, 5 pages.
Notice of Allowance, issued by the United States Patent and Trademark Office in connection with U.S. Appl. No. 12/056,190, dated Nov. 2, 2012, 5 pages.
Restriction Requirement, issued by the United States Patent and Trademark Office in connection with U.S. Appl. No. 12/056,225, dated Nov. 2, 2012, 5 pages.
Final Office Action, issued by the United States Patent and Trademark Office in connection with U.S. Appl. No. 12/135,066, dated Nov. 13, 2012, 9 pages.
Notice of Allowance, issued by the United States Patent and Trademark Office in connection with U.S. Appl. No. 12/113,863, dated Nov. 16, 2012, 5 pages.
Notice of Allowance, issued by the United States Patent and Trademark Office in connection with U.S. Appl. No. 12/056,211, dated Nov. 21, 2012, 5 pages.
Notice of Allowance, issued by the United States Patent and Trademark Office in connection with U.S. Appl. No. 12/868,531, dated Nov. 23, 2012, 5 pages.
Final Office Action, issued by the United States Patent and Trademark Office in connection with U.S. Appl. No. 12/846,242, dated Nov. 29, 2012, 14 pages.

(56) References Cited

OTHER PUBLICATIONS

Office Action, issued by the United States Patent and Trademark Office in connection with U.S. Appl. No. 12/913,102, dated Dec. 7, 2012, 7 pages.
Final Office Action, issued by the United States Patent and Trademark Office in connection with U.S. Appl. No. 12/544,958, dated Dec. 10, 2012, 16 pages.
Notice of Allowance, issued by the United States Patent and Trademark Office in connection with U.S. Appl. No. 12/853,197, dated Dec. 20, 2012, 5 pages.
Notice of Allowance, issued by the United States Patent and Trademark Office in connection with U.S. Appl. No. 12/056,190, dated Dec. 21, 2012, 14 pages.
Notice of Allowance, issued by the United States Patent and Trademark Office in connection with U.S. Appl. No. 12/056,211, dated Dec. 21, 2012, 10 pages.
Notice of Allowance, issued by the United States Patent and Trademark Office in connection with U.S. Appl. No. 12/122,262, dated Dec. 21, 2012, 19 pages.
Notice of Allowance, issued by the United States Patent and Trademark Office in connection with U.S. Appl. No. 12/135,074, dated Dec. 21, 2012, 12 pages.
Notice of Allowance, issued by the United States Patent and Trademark Office in connection with U.S. Appl. No. 12/199,557, dated Dec. 21, 2012, 14 pages.
Notice of Allowance, issued by the United States Patent and Trademark Office in connection with U.S. Appl. No. 12/199,596, dated Dec. 21, 2012, 17 pages.
Notice of Allowance, issued by the United States Patent and Trademark Office in connection with U.S. Appl. No. 12/200,813, dated Dec. 21, 2012, 9 pages.
Notice of Allowance, issued by the United States Patent and Trademark Office in connection with U.S. Appl. No. 12/853,213, dated Dec. 21, 2012, 10 pages.
Notice of Allowance, issued by the United States Patent and Trademark Office in connection with U.S. Appl. No. 12/868,531, dated Dec. 26, 2012, 2 pages.
Notice of Allowance, issued by the United States Patent and Trademark Office in connection with U.S. Appl. No. 12/113,863, dated Dec. 31, 2012, 5 pages.
Notice of Allowance, issued by the United States Patent and Trademark Office in connection with U.S. Appl. No. 12/199,583, dated Dec. 31, 2012, 10 pages.
Final Office Action, issued by the United States Patent and Trademark Office in connection with U.S. Appl. No. 12/182,874, dated Jan. 4, 2013, 17 pages.
Notice of Allowance, issued by the United States Patent and Trademark Office in connection with U.S. Appl. No. 12/199,583, dated Jan. 11, 2013, 11 pages.
Final Office Action, issued by the United States Patent and Trademark Office in connection with U.S. Appl. No. 12/056,225, dated Jan. 11, 2013, 11 pages.
Recertified IDS and Interview Summary, issued by the United States Patent and Trademark Office in connection with U.S. Appl. No. 12/853,197, dated Jan. 16, 2013, 6 pages.
Second Office Action, issued by the State Intellectual Property Office of P.R. China in connection with Patent Application No. 200880019166.0, dated Jun. 5, 2012, 8 pages.
Second Office Action, issued by the State Intellectual Property Office of P.R. China in connection with Patent Application No. 200880104982.1, dated Jun. 29, 2012, 5 pages.
Second Office Action, issued by the State Intellectual Property Office of P.R. China in connection with Patent Application No. 200880017883.X, dated Aug. 10, 2012, 9 pages.
English Translation of Office Action, issued by the Israel Patent Office in connection with Patent Application No. 203176, dated Sep. 27, 2012, 1 page.
English Translation of Office Action, issued by the Israel Patent Office in connection with Patent Application No. 203177, dated Sep. 27, 2012, 1 page.
Office Action, issued by the Japanese Patent Office in connection with Patent Application No. 2010-501190, dated Oct. 5, 2012, 5 pages.
English Translation of Office Action, issued by the Japanese Patent Office in connection with Patent Application No. 2010-506646, dated Oct. 23, 2012, 3 pages.
English Translation of Office Action, issued by the Israeli Patent Office in connection with Patent Application No. 201187, dated Nov. 27, 2012, 2 pages.
English Translation of Third Office Action, issued by the State Intellectual Property Office of P.R. China in connection with Patent Application No. 200880101500.7, dated Nov. 21, 2012, 5 pages.
Extended European Search Report, issued by the European Patent Office in connection with European Application No. 08796890.5-2319/2170161, dated Dec. 7, 2012, 9 pages.
Allen et al., "A Method of Removing Imaging Artifact from Continuous EEG Recorded during Functional MRI" Neuroimage, vol. 12, 230-239, (Aug. 2000), 12 pages.
Barreto et al., "Physiologic Instrumentation for Real-time Monitoring of Affective State of Computer Users," WSEAS International Conference on Instrumentation, Measurement Control, Circuits and Systems (IMCCAS), (2004), 6 pages.
Jung et al., "Analysis and Visualization of Single-Trial Event-Related Potentials," Human Brain Mapping vol. 14, 166-185 (2001), 20 pages.
Klimesch, "EEG alpha and theta oscillations reflect cognitive and memory performance a review and analysis,"Brain Research Reviews, vol. 29, 169-195, (1999), 27 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, 3-9 (Feb. 1971), 7 pages.
The Mathworks, Inc., "MATLAB Data Analysis: Version 7," p. 4-19 (2005), 3 pages.
Oberman et al., "EEG evidence for minor neuron activity during the observation of human and robot actionsAug. 29, 2012 Toward an analysis of the human qualities of interactive robots," Neurocomputing 70 (2007) 2194-2203, 10 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/-clemons/blogs/resonanceblog.pdf, (Mar. 28, 2007), 8 pages.
Palva et al., "Phase Synchrony Among Neuronal Oscillations in the Human Cortex," Journal of Neuroscience 25 (2005), 3962-3972, 11 pages.
Lachaux et al., "Measuring Phase Synchrony in Brain Signals," Human Brain Mapping 8 (1999), 194-208, 15 pages.
Final Office Action, issued by the United States Patent and Trademark Office in connection with U.S. Appl. No. 12/884,034, dated Oct. 23, 2013, 17 pages.
Notice of Allowance, issued by the United States Patent and Trademark Office in connection with U.S. Appl. No. 12/199,596, dated Nov. 6, 2013, 7 pages.
Final Office Action, issued by the United States Patent and Trademark Office in connection with U.S. Appl. No. 13/444,149, dated Nov. 19, 2013, 11 pages.
Non-Final Office Action, issued by the United States Patent and Trademark Office in connection with U.S. Appl. No. 12/122,253, dated Dec. 3, 2013, 16 pages.
Notice of Allowance, issued by the United States Patent and Trademark Office in connection with U.S. Appl. No. 12/199,596, dated Dec. 23, 2013, 7 pages.
Final Office Action, issued by the United States Patent and Trademark Office in connection with U.S. Appl. No. 13/105,774, dated Jan. 16, 2014, 11 pages.
English Translation of by Office Action, issued the Japanese Patent Office in connection with Patent Application No. 2010-520159, dated Oct. 1, 2013, 2 pages.
Extended European Search Report, issued by the European Patent Office in connection with European Application No. 08798799.6-1657/2180825, dated Nov. 4, 2013, 9 pages.

(56) References Cited

OTHER PUBLICATIONS

Coan et al., "Voluntary Facial Expression and Hemispheric Asymmetry Over the Frontal Cortex,"Psycophysiology (Nov. 2001), 912-924, 14 pages.
Duchowski, "A Breadth-First Survey of Eye-tracking Applications," Beahavior Research Methods, Instruments, and Computers (Nov. 2002), 455-470, 16 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Rothschild et al., "Predicting Memory for Components of TV Commercials from EEG," Journal of Consumer Research (Mar. 1990), p. 472-478, 8 pages.
Beaver et al., "Individual Differences in Reward Drive Predict Neural Responses to Images of Food", J. of Neuroscience, (May 10, 2006), 5160-5166, 7 pages.
Tapert et al., "Neural Response to Alcohol Stimuli in Adolescents With Alcohol Use Disorder", Arch Gen Psychiatry (Jul. 2003), 727-735, 9 pages.
Shandlen et al., "A Computational Analysis of the Relationship between Neuronal and Behavioral Responses to Visual Motion", The Journal ofNeuroscience, (Feb. 15, 1996) 1486-1510, 25 pages.
Cassanello et al., "Neuronal Responses to Moving Targets in Monkey Frontal Eye Fields", J Neurophysiol (Sep. 2008), 1544-1556, 16 pages.
Office Action, issued by the United States Patent and Trademark Office in connection with U.S. Appl. No. 12/056,211, dated Feb. 16, 2012, 15 pages.
Final Office Action, issued by the United States Patent and Trademark Office in connection with U.S. Appl. No. 12/056,190, dated Feb. 17, 2012, 22 pages.
Office Action, issued by the United States Patent and Trademark Office in connection with U.S. Appl. No. 12/122,253, dated Feb. 17, 2012, 20 pages.
Office Action, issued by the United States Patent and Trademark Office in connection with U.S. Appl. No. 12/182,874, dated Feb. 17, 2012, 15 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Office Action, issued by the United States Patent and Trademark Office in connection with U.S. Appl. No. 12/234,388, dated Oct. 12, 2011, 27 pages.
Office Action, issued by the United States Patent and Trademark Office in connection with U.S. Appl. No. 12/234,372, dated Oct. 13, 2011, 22 pages.
Office Action, issued by the United States Patent and Trademark Office in connection with U.S. Appl. No. 12/410,380, dated Oct. 19, 2011, 21 pages.
Office Action, issued by the United States Patent and Trademark Office in connection with U.S. Appl. No. 12/357,315, dated Oct. 26, 2011, 41 pages.
Office Action, issued by the United States Patent and Trademark Office in connection with U.S. Appl. No. 12/122,240, dated Oct. 27, 2011, 39 pages.
Final Office Action, issued by the United States Patent and Trademark Office in connection with U.S. Appl. No. 12/056,221, dated Nov. 28, 2011, 44 pages.
Office Action, issued by the United States Patent and Trademark Office in connection with U.S. Appl. No. 12/113,863, dated Dec. 22, 2011, 17 pages.
Office Action, issued by the United States Patent and Trademark Office in connection with U.S. Appl. No. 12/122,262, dated Dec. 22, 2011, 17 pages.
Office Action, issued by the United States Patent and Trademark Office in connection with U.S. Appl. No. 12/135,074, dated Dec. 22, 2011, 16 pages.
Office Action, issued by the United States Patent and Trademark Office in connection with U.S. Appl. No. 12/199,557, dated Dec. 22, 2011, 17 pages.
Office Action, issued by the United States Patent and Trademark Office in connection with U.S. Appl. No. 12/199,596, dated Dec. 22, 2011, 15 pages.
Office Action, issued by the United States Patent and Trademark Office in connection with U.S. Appl. No. 12/200,813, dated Dec. 22, 2011, 18 pages.
Office Action, issued by the United States Patent and Trademark Office in connection with U.S. Appl. No. 12/199,583, dated Dec. 29, 2011, 18 pages.
Final Office Action, issued by the United States Patent and Trademark Office in connection with U.S. Appl. No. 12/410,372, dated Jan. 3, 2012, 10 pages.
Final Office Action, issued by the United States Patent and Trademark Office in connection with U.S. Appl. No. 12/413,297, dated Jan. 4, 2012, 10 pages.
Office Action, issued by the United States Patent and Trademark Office in connection with U.S. Appl. No. 12/544,921, dated Jan. 9, 2012, 13 pages.
Office Action, issued by the United States Patent and Trademark Office in connection with U.S. Appl. No. 12/357,302, dated Jan. 17, 2012, 11 pages.
Office Action, issued by the United States Patent and Trademark Office in connection with U.S. Appl. No. 12/056,225, dated Jan. 20, 2012, 12 pages.
Final Office Action, issued by the United States Patent and Trademark Office in connection with U.S. Appl. No. 12/135,066, dated Jan. 24, 2012, 12 pages.
Office Action, issued by the United States Patent and Trademark Office in connection with U.S. Appl. No. 12/546,586, dated Feb. 1, 2012, 17 pages.
Restriction Requirement, issued by the United States Patent and Trademark Office in connection with U.S. Appl. No. 12/544,958, dated Feb. 10, 2012, 6 pages.
Final Office Action, issued by the United States Patent and Trademark Office in connection with U.S. Appl. No. 12/135,069, dated Feb. 14, 2012, 35 pages.
Final Office Action, issued by the United States Patent and Trademark Office in connection with U.S. Appl. No. 12/357,322, dated Feb. 14, 2012, 14 pages.
Decision of Rejection, issued by the State Intellectual Property Office of P.R. China in connection with Patent Application No. 200880104982.1, dated Sep. 23, 2011, 10 pages.
Extended European Search Report, issued by the European Patent Office in connection with European Application No. 11006934.1/2221, dated Oct. 25, 2011, 5 pages.
First Office Action, issued by the State Intellectual Property Office of P.R. China in connection with Patent Application No. 200880017883.X, dated Nov. 30, 2011, 16 pages.
Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.
Meriam Webster Online Dictionary definition for "tangible," available at http://www.merriam/webster.com/dictionary/tangible, 1 page.
Office Action, issued by the United States Patent and Trademark Office in connection with U.S. Application No. 12/868,531, on Mar. 1, 2012, 6 pages.
Office Action, issued by the United States Patent and Trademark Office in connection with U.S. Application No. 12/182,851, on Mar. 12, 2012, 14 pages.
Office Action, issued by the United States Patent and Trademark Office in connection with U.S. Appl. No. 12/608,685, dated Mar. 29, 2012, 17 pages.
Office Action, issued by the United States Patent and Trademark Office in connection with U.S. Appl. No. 12/846,242, dated Mar. 29, 2012, 15 pages.
Office Action, issued by the United States Patent and Trademark Office in connection with U.S. Appl. No. 12/234,388, dated Apr. 6, 2012, 6 pages.

(56) References Cited

OTHER PUBLICATIONS

Office Action, issued by the United States Patent and Trademark Office in connection with U.S. Appl. No. 12/357,315, dated Apr. 9, 2012, 17 pages.
Office Action, issued by the United States Patent and Trademark Office in connection with U.S. Appl. No. 12/544,958, dated May 2, 2012, 14 pages.
English Translation of Office Action, issued by the Israel Patent Office in connection with Patent Application No. 203176, dated Feb. 21, 2012, 2 pages.
English Translation of Office Action, issued by the Israel Patent Office in connection with Patent Application No. 203177, dated Mar. 1, 2012, 2 pages.
Second Office Action, issued by the State Intellectual Property Office of P.R. China in connection with Patent Application No. 200880101500.7, dated Apr. 5, 2012, 5 pages.
Padgett et al., "Categorical Perception in Facial Emotion Classification," In Proceedings of the 18th Annual Conference of the Cognitive Science Society, pp. 249-253 (1996), 5 pages.
De Gelder et al., "Categorical Perception of Facial Expressions: Categories and their Internal Structure,"Cognition and Emotion, vol. 11(1), pp. 1-23 (1997), 23 pages.
Bimler et al., "Categorical perception of facial expressions of emotion: Evidence from multidimensional scaling," Cognition and Emotion, vol. 15(5), pp. 633-658 (Sep. 2001), 26 pages.
Newell et al., "Categorical perception of familiar objects," Cognition, vol. 85, Issue 2, pp. 113-143 (Sep. 2002), 31 pages.
Meriam Webster Online Dictionary, Definition of Virtual Reality, available at http://www.meriamwebster.com/dictionary/virtual%20reality, 2 pages.
Griss et al., "Characterization of micromachined spiked biopotential electrodes," Biomedical Engineering, IEEE Transactions (Jun. 2002), 8 pages.
"User monitoring," Sapien Systems, available at http://web.archive.org/web/20030818043339/http:/www.sapiensystems.com/eyetracking.html, (Aug. 18, 2003), 1 page.
Sullivan et al., "A brain-machine interface using dry-contact, low-noise EEG sensors," In Proceedings of the 2008 IEEE International Symposium on Circuits and Systems, (May 18, 2008), 4 pages.
Final Office Action, issued by the United States Patent and Trademark Office in connection with U.S. Appl. No. 12/056,211, dated Jul. 8, 2011, 16 pages.
Office Action, issued by the United States Patent and Trademark Office in connection with U.S. Appl. No. 12/056,211, dated Jan. 7, 2011, 19 pages.
Office Action issued by the United States Patent and Trademark Office in connection with U.S. Appl. No. 12/056,221, dated Apr. 15, 2011, 24 pages.
Final Office Action, issued by the United States Patent and Trademark Office in connection with U.S. Appl. No. 12/113,863, dated Jun. 9, 2011, 12 pages.
Office Action, issued by the United States Patent and Trademark Office in connection with U.S. Appl. No. 12/113,863, dated Dec. 27, 2010, 15 pages.
Final Office Action, issued by the United States Patent and Trademark Office in connection with U.S. Appl. No. 12/113,870, dated Apr. 21, 2011, 10 pages.
Office Action, issued by the United States Patent and Trademark Office in connection with U.S. Appl. No. 12/113,870, dated Dec. 3, 2010, 12 pages.
Office Action, issued by the United States Patent and Trademark Office in connection with U.S. Appl. No. 12/122,240, dated Jun. 10, 2011, 12 pages.
Final Office Action, issued by the United States Patent and Trademark Office in connection with U.S. Appl. No. 12/122,262, dated May 26, 2011, 15 pages.
Office Action, issued by the United States Patent and Trademark Office in connection with U.S. Appl. No. 12/122,262, dated Dec. 9, 2010, 13 pages.
Final Office Action, issued by the United States Patent and Trademark Office in connection with U.S. Appl. No. 12/135,066, dated Jan. 21, 2011, 16 pages.
Office Action, issued by the United States Patent and Trademark Office in connection with U.S. Appl. No. 12/135,066, dated Oct. 28, 2010, 14 pages.
Notice of Panel Decision from Pre-Appeal Brief Review, issued by the United States Patent and Trademark Office in connection with U.S. Appl. No. 12/135,066, dated May 31, 2011, 2 pages.
Office Action, issued by the United States Patent and Trademark Office in connection with U.S. Appl. No. 12/135,074, dated Dec. 23, 2010, 14 pages.
Final Office Action, issued by the United States Patent and Trademark Office in connection with U.S. Appl. No. 12/135,074, dated Jun. 9, 2011, 10 pages.
Final Office Action, issued by the United States Patent and Trademark Office in connection with U.S. Appl. No. 12/182,874, dated Jul. 7, 2011, 14 pages.
Office Action, issued by the United States Patent and Trademark Office in connection with U.S. Appl. No. 12/182,874, dated Dec. 27, 2010, 17 pages.
Office Action, issued by the United States Patent and Trademark Office in connection with U.S. Appl. No. 12/199,557, dated Dec. 27, 2010, 14 pages.
Final Office Action, issued by the United States Patent and Trademark Office in connection with U.S. Appl. No. 12/199,557, dated Jun. 9, 2011, 12 pages.
Final Office Action, issued by the United States Patent and Trademark Office in connection with U.S. Appl. No. 12/199,583, dated Jun. 21, 2011, 14 pages.
Office Action, issued by the United States Patent and Trademark Office in connection with U.S. Appl. No. 12/199,583, dated Dec. 27, 2010, 17 pages.
Final Office Action, issued by the United States Patent and Trademark Office in connection with U.S. Appl. No. 12/199,596, dated Jun. 14, 2011, 13 pages.
Office Action, issued by the United States Patent and Trademark Office in connection with U.S. Appl. No. 12/199,596, dated Dec. 27, 2010, 17 pages.
Final Office Action, issued by the United States Patent and Trademark Office in connection with U.S. Appl. No. 12/200,813, dated Jul. 6, 2011, 13 pages.
Office Action, issued by the United States Patent and Trademark Office in connection with U.S. Appl. No. 12/200,813, dated Dec. 27, 2010, 14 pages.
Office Action, issued by the United States Patent and Trademark Office in connection with U.S. Appl. No. 12/234,372, dated Jun. 7, 2011, 10 pages.
Final Office Action, issued by the United States Patent and Trademark Office in connection with U.S. Appl. No. 12/135,069, dated Feb. 17, 2011, 32 pages.
Office Action, issued by the United States Patent and Trademark Office in connection with U.S. Appl. No. 12/135,069, dated Oct. 29, 2010, 21 pages.
Office Action, issued by the United States Patent and Trademark Office in connection with U.S. Appl. No. 12/357,315, dated May 4, 2011, 9 pages.
Office Action, issued by the United States Patent and Trademark Office in connection with U.S. Appl. No. 12/410,380, dated Jun. 7, 2011, 9 pages.
Office Action, issued by the United States Patent and Trademark Office in connection with U.S. Appl. No. 12/413,297, dated Jul. 18, 2011, 9 pages.
Office Action, issued by the United States Patent and Trademark Office in connection with U.S. Application No. 12/608,685, dated Jul. 12, 2011, 15 pages.
Office Action, issued by the United States Patent and Trademark Office in connection with U.S. Appl. No. 12/056,190, dated Aug. 10, 2011, 28 pages.
Office Action, issued by the United States Patent and Trademark Office in connection with U.S. Appl. No. 12/357,322, dated Aug. 23, 2011, 12 pages.

(56) References Cited

OTHER PUBLICATIONS

Office Action, issued by the United States Patent and Trademark Office in connection with U.S. Appl. No. 12/135,069, dated Aug. 26, 2011, 33 pages.
Restriction Requirement, issued by the United States Patent and Trademark Office in connection with U.S. Appl. No. 12/122,253, dated Sep. 2, 2011, 7 pages.
Office Action, issued by the United States Patent and Trademark Office in connection with U.S. Appl. No. 12/410,372, dated Sep. 12, 2011, 12 pages.
Restriction Requirement, issued by the United States Patent and Trademark Office in connection with U.S. Appl. No. 12/182,851, dated Sep. 12, 2011, 7 pages.
Office Action, issued by the United States Patent and Trademark Office in connection with U.S. Appl. No. 12/135,066, dated Sep. 29, 2011, 37 pages.
Restriction Requirement, issued by the United States Patent and Trademark Office in connection with U.S. Appl. No. 12/056,225, dated Oct. 3, 2011, 6 pages.
International Preliminary Report on Patentability, issued by the International Bureau of WIPO in connection with International Application No. PCT/US08/058264, dated Sep. 29, 2009, 1 page.
International Search Report, issued by the International Searching Authority in connection with International Application No. PCT/US08/058264, dated Aug. 1, 2008, 2 pages.
Written Opinion, issued by the International Searching Authority in connection with International Application No. PCT/US08/058264, dated Aug. 1, 2008, 5 pages.
International Preliminary Report on Patentability, issued by the International Bureau ofWIPO in connection with International Application No. PCT/US08/062273, dated Nov. 3, 2009, 1 page.
International Search Report, issued by the International Searching Authority in connection with International Application No. PCT/US08/062273, dated Sep. 5, 2008, 2 pages.
Written Opinion, issued by the International Searching Authority in connection with International Application No. PCT/US08/062273, dated Sep. 5, 2008, 4 pages.
International Preliminary Report on Patentability, issued by the International Bureau ofWIPO in connection with International Application No. PCT/US08/062275, dated Nov. 3, 2009, 1 page.
International Search Report, issued by the International Bureau in connection with International Application No. PCT/US08/062275, dated Sep. 22, 2008, 1 page.
Written Opinion, issued by the International Bureau in connection with International Application No. PCT/USOS/062275, dated Sep. 22, 2008, 6 pages.
International Preliminary Report on Patentability, issued by the International Bureau ofWIPO in connection with International Application No. PCT/US08/063984, dated Nov. 17, 2009, 1 page.
International Search Report, issued by the International Bureau in connection with International Application No. PCT/USOS/063984, dated Sep. 29, 2008, 2 pages.
Written Opinion, issued by the International Bureau in connection with International Application No. PCT/USOS/063984, dated Sep. 29, 2008, 3 pages.
International Preliminary Report on Patentability, issued by the International Bureau ofWIPO in connection with International Application No. PCT/US08/063989, dated Nov. 17, 2009, 1 page.
International Search Report, issued by the International Bureau in connection with International Application No. PCT/US08/063989, dated Jul. 17, 2008, 1 page.
Written Opinion, issued by the International Bureau in connection with International Application No. PCT/US08/063989, dated Jul. 17, 2008, 4 pages.
International Preliminary Report on Patentability, issued by the International Bureau ofWIPO in connection with International Application No. PCT/US08/066166, dated Dec. 7, 2009, 1 page.
International Search Report, issued by the International Bureau in connection with International Application No. PCT/US08/066166, dated Aug. 25, 2008, 1 page.
Written Opinion, issued by the International Bureau in connection with International Application No. PCT/US08/066166, dated Aug. 25, 2008, 6 pages.
International Preliminary Report on Patentability, issued by the International Bureau ofWIPO in connection with International Application No. PCT/US08/071639, dated Feb. 2, 2010, 1 page.
International Search Report, issued by the International Bureau in connection with International Application No. PCT/US08/071639, dated Oct. 22, 2008, 1 page.
Written Opinion, issued by the International Bureau in connection with International Application No. PCT/US08/071639, dated Oct. 22, 2008, 4 pages.
International Preliminary Report on Patentability, issued by the International Bureau ofWIPO in connection with International Application No. PCT/US08/074467, dated Mar. 2, 2010, 1 page.
International Search Report, issued by the International Bureau in connection with International Application No. PCT/USOS/074467, dated Nov. 17, 2008, 2 pages.
Written Opinion, issued by the International Bureau in connection with International Application No. PCT/US08/074467, dated Nov. 17, 2008,4 pages.
International Preliminary Report of Patentability, issued by the International Bureau in connection with International Application No. PCT/US10/021535, dated Jul. 26, 2011, 1 page.
International Search Report, issued by the International Bureau in connection with International Application No. PCT/US10/021535, dated Mar. 23, 2010, 3 pages.
Written Opinion, issued by the International Bureau in connection with International Application No. PCT/US10/021535, dated Mar. 23, 2010, 4 pages.
International Preliminary Report of Patentability, issued by the International Bureau in connection with International Application No. PCT/US09/065368, dated Jun. 23, 2011, 2 pages.
International Search Report, issued by the International Bureau in connection with International Application No. PCT/US09/065368, dated Jan. 21, 2010, 3 pages.
Written Opinion, issued by the International Bureau in connection with International Application No. PCT/US09/065368, dated Jan. 21, 2010, 7 pages.
Extended European Search Report, issued by the European Patent Office in connection with European Application No. 08744383.4-2221/2130146, dated Jul. 27, 2011, 5 pages.
Extended European Search Report, issued by the European Patent Office in connection with European Application No. 10173095.0-2221, dated Dec. 17, 2010, 3 pages.
Extended European Search Report, issued by the European Patent Office in connection with European Application No. 10189294.1-2221, dated Mar. 21, 2011, 7 pages.
First Office Action, issued by the State Intellectual Property Office of P.R. China in connection with Patent Application No. 200880104982.1, dated January 25, 2011, 15 pages.
First Office Action, issued by the State Intellectual Property Office of P.R. China in connection with Patent Application No. 2008801015007, dated May 25, 2011, 8 pages.
First Office Action, issued by the State Intellectual Property Office of P.R. China in connection with Patent Application No. 200880019166.0, dated Jul. 22, 2011, 16 pages.
Edgar et al., "Digital Filters in ERP Research," in Event-Related Potentials: A Methods Handbook, pp. 85-113, (Todd C. Handy, ed., 2005), 15 pages.
Simon-Thomas et al., "Behavioral and Electrophysiological Evidence of a Right Hemisphere Bias for the Influence ofNegative Emotion on Higher Cognition," Journal of Cognitive Neuroscience, pp. 518-529, Massachusetts Institute of Technology (2005), 12 pages.
Friedman et al., "Event-Related Potential (ERP) Studies of Memory Encoding and Retrieval: A Selective Review," Microscopy Research and Technique 51:6-26, Wiley-Less, Inc. (2000), 23 pages.
Gaillard, "Problems and Paradigms in ERP Research," Biological Psychology, Elsevier Science Publisher B.V. (1988), 10 pages.
Hopf et al., "Neural Sources of Focused Attention in Visual Search," Cerebral Cortex, 10:1233-1241, Oxford University Press, (Dec. 2000), 9 pages.

(56) References Cited

OTHER PUBLICATIONS

Swick et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Luck et al., "The speed of visual attention in schizophrenia: Electrophysiological and behavioral evidence,"Schizophrenia Research, pp. 174-195, Elsevier B.V., www.sciencedirect.com, (2006), 22 pages.
Makeig et al., "Mining event-related brain dynamics," Trends in Cognitive Sciences, vol. 8, No. 5, (May 2004), www.sciencedirect.com, 7 pages.
Herrmann et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.
Knight, "Consciousness Unchained: Ethical Issues and the Vegetative and minimally Conscious State," The American Journal ofBioethics, 8:9, 1-2, http://dx.doi.org/10.1080/15265160802414524, (Sep. 1, 2008), 3 pages.
Kishiyama et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Paller et al., "Validating neural correlates of familiarity," Trends in Cognitive Sciences, vol. 11, No. 6, www.sciencedirect.com, (May 2, 2007), 8 pages.
Picton et al., "Guidelines for using human event-related potentials to study cognition: Recording standards and publication criteria," Psychophysiology, pp. 127-152, Society for Psychophysiological Research, (2000), 26 pages.
Yamaguchi et al., "Rapid-Prefrontal-Hippocampal Habituation to Novel Events," The Journal of Neuroscience, pp. 5356-5363, Society for Neuroscience, (Apr. 29, 2004), 8 pages.
Rugg et al., "Event-related potentials and recognition memory," Trends in Cognitive Sciences, vol. 11, No. 6, www.sciencedirect.com , (May 3, 2007), 7 pages.
Rugg et al., "The ERP and cognitive psychology: conceptual issues," (Sep. 1996), 7 pages.
Keren et al., "Saccadic spike potentials in gamma-band EEG: Characterization, detection and suppression," Neuroimage, http://dx.doi:10.1016/j.neuroimage.2009.10.057, (Oct. 2009), 16 pages.
Kishiyama et al., "Socioeconomic Disparities Affect Prefrontal Function in Children," Journal of Cognitive Neuroscience, pp. 1106-1115, Massachusetts Institute of Technology, (2008), 10 pages.
Spencer, "Averaging, Detection, and Classification of Single-Trial ERPs," in Event-Related Potentials: A Methods Handbook, pp. 209-227, (Todd C. Handy, ed., 2005), 10 pages.
Srinivasan, "High-Resolution EEG: Theory and Practice," in Event-Related Potentials: A Methods Handbook, pp. 167-188, (Todd C. Handy, ed., 2005), 12 pages.
Taheri et al., "A dry electrode for EEG recording," Electroencephalography and clinical Neurophysiology, pp. 376-383, Elsevier Science Ireland Ltd. (1994), 8 pages.
Talsma et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Davidson et al., "The functional neuroanatomy of emotion and affective style," Trends in Cognitive Sciences, vol. 3, No. 1, (Jan. 1999), 11 pages.
Vogel et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
Rizzolatti et al., "The Mirror-Neuron System," Annu. Rev. Neurosci., vol. 27, pp. 169-192, (Mar. 5, 2004), 30 pages.
Woldorf, "Distortion of ERP averages due to overlap from temporally adjacent ERPs: Analysis and correction," Psychophysiology, Society for Psychophysiological Research, Cambridge University Press (1993), 22 pages.
Woodman et al., "Serial Deployment of Attention During Visual Search," Journal of Experimental Psychology: Human Perception and Performance, vol. 29, No. 1, pp. 121-138, American Physiological Association (2003 ), 18 pages.
Filler, "MR Neurography and Diffusion Tensor Imaging: Origins, History & Clinical Impact of the first 50,000 Cases With an Assortment of Efficacy and Utility in a Prospective 5,000 Patent Study Group,"Institute for Nerve Medicine, (Nov. 7, 2008), 56 pages.
Yuval-Greenberg et al., "Transient Induced Gamma-Bands Response in EEG as a Manifestation of Miniature Saccades," Neuron, vol. 58, pp. 429-441, Elsevier Inc. (May 8, 2008), 13 pages.
Knight et al., "Prefrontal cortex regulates inhibition and excitation in distributed neural networks," Acta Psychologica vol. 101, pp. 159-178, Elsevier (1999), 20 pages.
Gargiulo et al., "A Mobile EEG System With Dry Electrodes," (Nov. 2008), 4 pages.
Buschman et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.
Buschman et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.
Lui et al., "Marketing Strategies in Virtual Worlds," The Data Base for Advances in Information Systems, vol. 38, No. 4, pp. 77-80, (Nov. 2007), 4 pages.
Cheng et al. "Gender Differences I the Mu Rhythm of the Human Minor-Neuron System," PLos One, vol. 3, Issue 5, www.plosone.org, (May 2008), 7 pages.
Fogelson et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.
D'Esposito, "From cognitive to neural models of working memory," Phil. Trans. R. Soc. B, doi: 10.1098/rstb.2007.2086, (Mar. 30, 2007), 12 pages.
Dien et al., "Application of Repeated Measures ANOVA to High-Dens Dataset: A Review and Tutorial," in Event-Related Potentials: A Methods Handbook, pp. 57-82, (Todd C. Handy, ed., 2005), 14 pages.
Neurofocus—Neuroscientific Analysis for Audience Engagement, accessed on Jan. 8, 2010 at http://web.archive.org/web/20080621114525/www.neurofocus.com/BrandImage.htm, (2008), 2 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Hazlett et al., "Emotional Response to Television Commercials: Facial EMG vs. Self-Report," Journal of Advertising Research, (Apr. 1999), 17 pages.
Makeig et al., "Dynamic Brain Sources of Visual Evoked Responses," Science, vol. 295, www.sciencemag.org, (Jan. 25, 2002), 5 pages.
Lewis et al., "Market Researchers make Increasing use of Brain Imaging," ACNR, vol. 5, No. 3, pp. 36-37, (Jul./Aug. 2005), 2 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Haq, "This Is Your Brain on Advertising," BusinessWeek, Market Research, (Oct. 8, 2007), 3 pages.
EEG Protocols, "Protocols for EEG Recording," retrieved from the Internet on Aug. 23, 2011, http://www.q-metrx.com/EEDrecordingProtocols.pdf, (Nov. 13, 2007), 3 pages.

(56) References Cited

OTHER PUBLICATIONS

Aaker et al., "Warmth in Advertising: Measurement, Impact, and Sequence Effects," Journal of Consumer Research, vol. 12, No. 4, pp. 365-381, (Mar. 1986), 17 pages.
Belch et al., "Psychophysiological and cognitive Response to Sex in Advertising," Advances in Consumer Research, vol. 9, pp. 424-427, (1982), 6 pages.
Ruchkin et al., "Modality-specific processing streams in verbal working memory: evidence from spatiotemporal patterns of brain activity," Cognitive Brain Research, vol. 6, pp. 95-113, Elsevier, (1997), 19 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Braeutigam, "Neuroeconomics—From neural systems to economic behavior," Brain Research Bulletin, vol. 67, pp. 355-360, Elsevier, (2005), 6 pages.
Lee et al., "What is 'neuromarketing'? A discussion and agenda for future research," International Journal of Psychophysiology, vol. 63, pp. 199-204, Elsevier (2006), 6 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.
Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.
Bagozzi et al., "The Role of Emotions in Marketing," Journal of the Academy of Marketing Science, vol. 27, No. 2, pp. 184-206, Academy of Marketing Science (1999), 23 pages.
Blakeslee, "If You Have a 'Buy Button' in Your Brain, What Pushes It?" The New York Times, www.nytimes.com, (Oct. 19, 2004), 3 pages.
Kay et al., "Identifying natural images from human brain activity," Nature, vol. 452, pp. 352-356, Nature Publishing Group, (Mar. 20, 2008), 5 pages.
Anonymous, "Functional magnetic resonance imaging," retrieved online from Wikipedia, the Free Encyclopedia on Sep. 18, 2017, at https://en.wikipedia.org/wild/Functional_magnetic_resonance_imaging, (Last edited Aug. 17, 2017), 24 pages.
Osborne, "Embedded Watermarking for image Verification in Telemedicine," Thesis submitted for the degree of Doctor of Philosophy, Electrical and Electronic Engineering, University of Adelaide (2005), 219 pages.
Nielsen, "Neuroinformatics in Functional Neuroimaging," Informatics and Mathematical Modeling, Technical University of Denmark, (Aug. 30, 2002), 241 pages.
Arousal in Sport, in Encyclopedia of Applied Psychology, vol. 1, p. 159, retrieved from Google Books, (Spielberger, ed., Elsevier Academic Press, 2004), 1 page.
Ziegenfuss, "Neuromarketing: Advertising Ethical & Medical Technology," The Brownstone Journal, vol. XII, Boston University, pp. 69-73, (May 2005), 9 pages.
Zyga, "A Baseball Cap That Can Read Your Mind," PhysOrg.com, located at www.physorg.com/news130152277.html, (May 16, 2008), 11 pages.
Lekakos, "Personalized Advertising Services Through Hybrid Recommendation Methods: The Case of Digital Interactive Television," Department of informatics, Cyprus University, (2004), 11 pages.
Yap et al., "TIMER: Tensor Image Morphing for Elastic Registration," NeuroImage, vol. 47, (May 3, 2009), 15 pages.
Clifford, "Billboards That Look Back," The New York Times, NYTimes.com, available at http://www.nytimes.com/2008/05/31/business/media/31billboard.html, (May 31, 2008), 4 pages.
Barcelo et al., "Prefrontal Modulation of Visual Processing in Humans,"Nature Neuroscience, vol. 3, No. 4, Apr. 2000, pp. 399-403.
Canolty et al., "High Gamma Power Is Phase-Locked to Theta Oscillations in Human Neocortex," Science, vol. 313, Sep. 15, 2006, pp. 1626-1628.
Engel et al., "Dynamic Predictions: Oscillations and Synchrony in Top-Down Processing," Macmillan Magazines Ltd, vol. 2, Oct. 2001, pp. 704-716.
Fries, "A Mechanism for Cognitive Dynamics: Neuronal Communication Through Neuronal Coherence," Trends in Cognitive Sciences, vol. 9, No. 10, Oct. 2005, 7 pages.
Gazzaley et al., "Top-down Enhancement and Suppression of the Magnitude and Speed ofNeural Activity," Journal of Cognitive Neuroscience, vol. 17, No. 3, pp. 507-517.
Hartikainen et al., "Emotionally Arousing Stimuli Compete with Attention to Left Hen'lispace," Editorial Manager(tm) for NeuroReport, Manuscipt Draft, Manuscript No.
Knight, "Contribution of Human Hippocampal Region to Novelty Detection," Nature, vol. 383, Sep. 19, 1996, p. 256-259.
Knight, "Decreased Response to Novel Stimuli After Prefrontal Lesions in Man," Electroencephalography and Clinical Neurophysiology, vol. 59, 1984, pp. 9-20.
Miltner et al., "Coherence ofGannna-band EEG Activity as a Basis for Associative Learning," Nature, vol. 397, Feb. 4, 1999, pp. 434-436.
Office Action, issued by the United States Patent and Trademark Office in connection with U.S. Appl. No. 13/730,541, dated Jan. 30, 2014, 12 pages.
Office Action, issued by the United States Patent and Trademark Office in connection with U.S. Appl. No. 12/135,066, dated Jun. 21, 2012, 10 pages.
Advisory Action, issued by the United States Patent and Trademark Office in connection with U.S. Appl. No. 12/546,586, dated Dec. 22, 2014, 3 pages.
First Examination Report, issued by the European Patent Office in connection with European Application No. 108796890.5, dated Sep. 29, 2016, 4 pages.
Final Office Action, issued by the United States Patent and Trademark Office in connection with U.S. Appl. No. 13/945,357, dated Nov. 1, 2016, 22 pages.
Advisory Action, issued by the United States Patent and Trademark Office in connection with U.S. Appl. No. 12/410,372, dated Nov. 7, 2016, 3 pages.
Examiner's Answer, issued by the United States Patent and Trademark Office in connection with U.S. Appl. No. 12/234,372, dated Nov. 14, 2016, 18 pages.
Examiner's Answer, issued by the United States Patent and Trademark Office in connection with U.S. Appl. No. 12/608,685, dated Nov. 14, 2016, 10 pages.
Final Office Action, issued by the United States Patent and Trademark Office in connection with U.S. Appl. No. 12/884,034, dated Nov. 29, 2016, 27 pages.
Final Office Action, issued by the United States Patent and Trademark Office in connection with U.S. Appl. No. 12/410,380, dated Dec. 15, 2016, 31 pages.
Non-Final Office Action, issued by the United States Patent and Trademark Office in connection with U.S. Appl. No. 13/708,344, dated Jan. 26, 2017, 52 pages.
Examiner's Answer, issued by the United States Patent and Trademark Office in connection with U.S. Appl. No. 13/965,805, dated Jan. 31, 2017, 25 pages.
Final Office Action, issued by the United States Patent and Trademark Office in connection with U.S. Appl. No. 12/413,297, dated Feb. 9, 2017, 7 pages.
Advisory Action, issued by the United States Patent and Trademark Office in connection with U.S. Appl. No. 12/884,034, dated Mar. 2, 2017, 14 pages.
Decision on Appeal, issued by the United States Patent and Trademark Office in connection with U.S. Appl. No. 12/122,253, dated Mar. 31, 2017, 37 pages.
Non-Final Office Action, issued by the United States Patent and Trademark Office in connection with U.S. Appl. No. 13/708,525, dated Apr. 27, 2017, 45 pages.

(56) References Cited

OTHER PUBLICATIONS

Examiner's Answer, issued by the United States Patent and Trademark Office in connection with U.S. Appl. No. 12/410,372, dated May 25, 2017, 2017, 9 pages.
Decision on Appeal, issued by the United States Patent and Trademark Office in connection with U.S. Appl. No. 12/546,586, dated Jun. 5, 2017, 39 pages.
Final Office Action, issued by the United States Patent and Trademark Office in connection with U.S. Appl. No. 13/708,344, dated Jun. 29, 2017, 38 pages.
Non-Final Office Action, issued by the United States Patent and Trademark Office in connection with U.S. Appl. No. 13/945,357, dated Jul. 6, 2017, 17 pages.
Decision on Appeal, issued by the United States Patent and Trademark Office in connection with U.S. Appl. No. 12/113,870, dated Jul. 13, 2017, 12 pages.
Final Office Action, issued by the United States Patent and Trademark Office in connection with U.S. Appl. No. 13/708,525, dated Aug. 14, 2017, 38 pages.
Examiner's Answer, issued by the United States Patent and Trademark Office in connection with U.S. Appl. No. 12/410,380, dated Aug. 18, 2017, 2017, 11 pages.
Non-Final Office Action, issued by the United States Patent and Trademark Office in connection with U.S. Appl. No. 12/546,586, dated Sep. 19, 2017, 43 pages.
Notice of Allowance, issued by the United States Patent and Trademark Office in connection with U.S. Appl. No. 12/113,870, dated Sep. 26, 2017, 51 pages.
Advisory Action, issued by the United States Patent and Trademark Office in connection with U.S. Appl. No. 13/708,344, dated Oct. 2, 2017, 5 pages.
Final Office Action, issued by the United States Patent and Trademark Office in connection with U.S. Appl. No. 13/945,357, dated Oct. 20, 2017, 16 pages.
Advisory Action, issued by the United States Patent and Trademark Office in connection with U.S. Appl. No. 13/708,525, dated Oct. 26, 2017, 4 pages.
Examiner's Answer, issued by the United States Patent and Trademark Office in connection with U.S. Appl. No. 12/413,297, dated Oct. 31, 2017, 2017, 68 pages.
Non-Final Office Action, issued by the United States Patent and Trademark Office in connection with U.S. Appl. No. 15/299,752, dated Nov. 3, 2017, 131 pages.
Non-Final Office Action, issued by the United States Patent and Trademark Office in connection with U.S. Appl. No. 12/884,034, dated Nov. 15, 2017, 49 pages.
Decision on Appeal, issued by the United States Patent and Trademark Office in connection with U.S. Appl. No. 13/730,541, dated Dec. 6, 2017, 14 pages.
Non-Final Office Action, issued by the United States Patent and Trademark Office in connection with U.S. Appl. No. 12/546,586, dated Dec. 28, 2017, 23 pages.
Decision on Appeal, issued by the United States Patent and Trademark Office in connection with U.S. Appl. No. 12/608,685, dated Jan. 29, 2018, 11 pages.
English Translation of Notice Prior to Allowance, issued by the Israeli Patent Office in connection with Patent Application No. 201187, dated Feb. 14, 2017, 1 page.
Communication Pursuant to Article 94(3), issued by the European Patent Office in connection with European Application No. 08744383.4-1958, dated Apr. 19, 2017, 6 pages.
Summons to Attend Oral Proceedings Pursuant to Rule 115(1) EPC, issued by the European Patent Office in connection with European Patent Application No. 08796890.5, dated Jul. 3, 2017, 3 pages.
English Translation of First Examination Report, issued by the Indian Patent Office in connection with Indian Patent Application No. 6145/CHENP/2009, dated Aug. 16, 2017, 6 pages.
English Translation of First Examination Report, issued by the Indian Patent Office in connection with Indian Patent Application No. 4438/KOLNP/2009, dated Sep. 25, 2017, 7 pages.
Ganel et al., "The Relationship Between fMRI Adapation and Repetition Priming," NeuroImage, Jul. 18, 2006, pp. 1434-1440, 9 pages.
Hall, Bruce F., "A New Model for Measuring Advertising Effectiveness," Journal of Advertising Research, Mar.-Apr. 2002, 10 pages.
Decision on Appeal, issued by the United States Patent and Trademark Office in connection with U.S. Appl. No. 13/730,564, dated Feb. 2, 2018, 10 pages.
Decision on Appeal, issued by the United States Patent and Trademark Office in connection with U.S. Appl. No. 13/730,511, dated Mar. 1, 2018, 14 pages.
Decision on Appeal, issued by the United States Patent and Trademark Office in connection with U.S. Appl. No. 13/730,550, dated Mar. 27, 2018, 13 pages.
Final Office Action, issued by the United States Patent and Trademark Office in connection with U.S. Appl. No. 12/884,034, dated May 3, 2018, 46 pages.
Non-Final Office Action, issued by the United States Patent and Trademark Office in connection with U.S. Appl. No. 13/708,525, dated May 18, 2018, 31 pages.
Communication Under Rule 71(3) EPC, issued by the European Patent Office in connection with European Application No. 08796890.5, dated Mar. 16, 2018, 43 pages.
English Translation of First Examination Report, issued by the Indian Patent Office in connection with Indian Patent Application No. 4441/KOLNP/2009, dated May 21, 2018, 5 pages.
Notice of Allowance, issued by the United States Patent and Trademark Office in connection with U.S. Appl. No. 13/730,541, dated Jun. 27, 2018, 62 pages.
Notice of Allowance, issued by the United States Patent and Trademark Office in connection with U.S. Appl. No. 13/730,564, dated Jun. 27, 2018, 69 pages.
Final Office Action, issued by the United States Patent and Trademark Office in connection with U.S. Appl. No. 12/546,586, dated Jun. 28, 2018, 22 pages.

* cited by examiner

Stimulus Attributes Data Model 201

| Video Game 203 | Rating 205 | Time Span 207 | Audience 209 | Demography 211 | ... |

Stimulus Purpose Data Model 213

| Intent 215 | Objectives 217 | Candidate Location Information 219 | ... |

Stimulus Attributes Data Model 221

| Creation Attributes 223 | Ownership Attributes 225 | Broadcast Attributes 227 | Statistical, Demographic, And Survey Based Identifiers 229 |

| Dataset Data Model 301 | | | | |
|---|---|---|---|---|
| Experiment Name 303 | Client Attributes 305 | Subject Pool 307 | Logistics Information 309 | Stimulus Material 311 |

| Subject Attributes Data Model 315 | | |
|---|---|---|
| Subject Name 317 | Demographic Attributes 319 | Contact Information 321 |

| Neuro-Feedback Association Data Model 325 | |
|---|---|
| Experiment Protocols 327 | Modalities included 329 | Experiment Design Parameters 333 |

| Neuro-Feedback Association Data Model 325 | | |
|---|---|---|
| Experiment Protocols 327 | Modalities included 329 | Experiment Design Parameters 333 |

| Data Collection Data Model 337 | | | |
|---|---|---|---|
| Recording Attributes 339 | Equipment Attributes 341 | Modalities Recorded 343 | Data Storage Attributes 345 |

| Preset Query Data Model 349 | | | |
|---|---|---|---|
| Query Name 351 | Accessed Data Collection 353 | Access Security Attributes 355 | Refresh Attributes 357 |

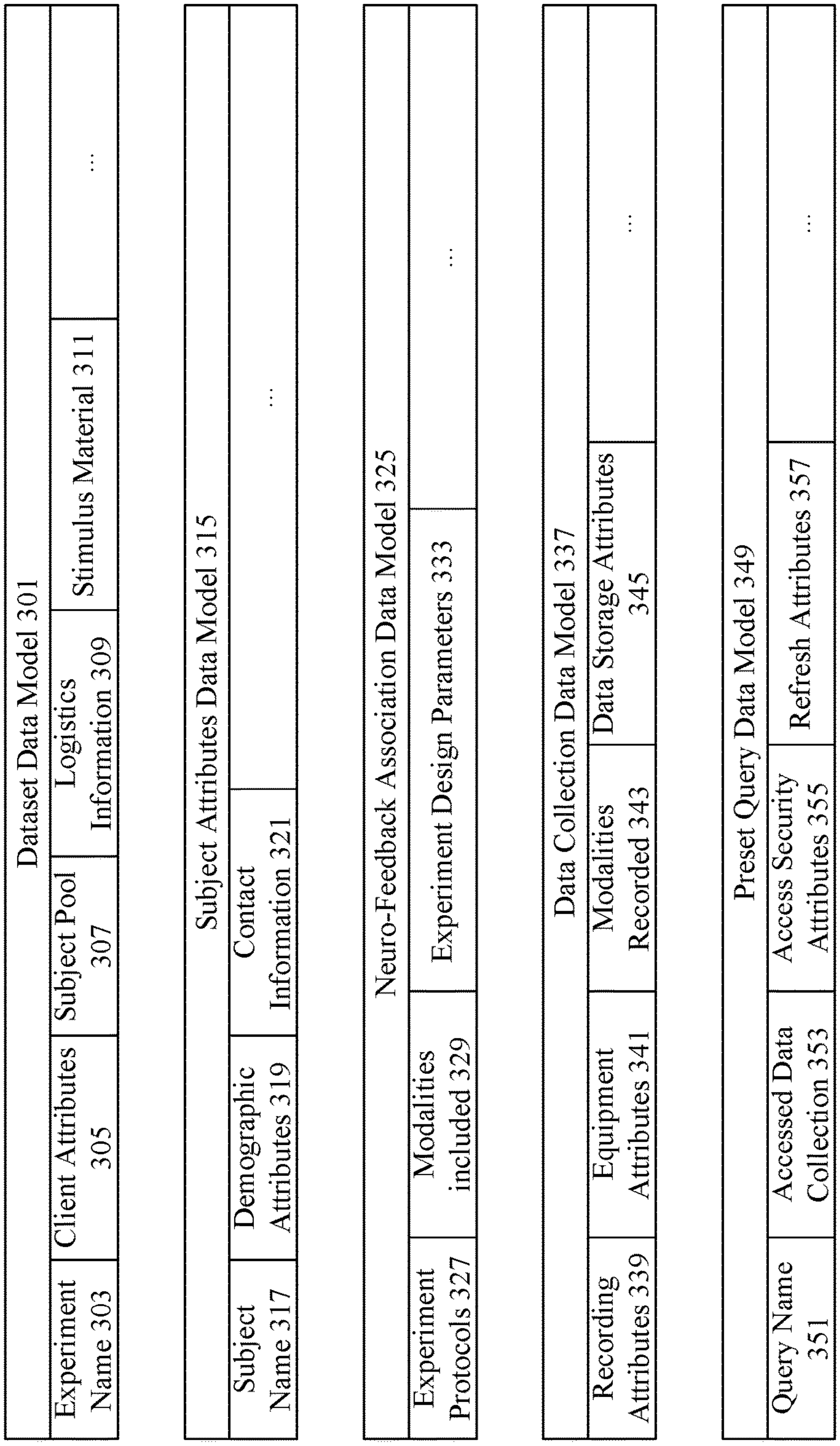

Figure 3

| Subject Attributes Queries 415 | | |
|---|---|---|
| Location 417 | Demographic Attributes 419 | Session Information 421 | ... |

| Experimental Design Queries 425 | | |
|---|---|---|
| Experiment Protocols 427 | Product Category 429 | Surveys Included 431 | Stimulus Used 433 | ... |

| Response Assessment Queries 437 | | |
|---|---|---|
| Attention Score 439 | Emotion Score 441 | Retention Score 443 | Effectiveness Score 445 |

| Client Assessment Summary Reports 501 | | |
|---|---|---|
| Effectiveness 503 | Component Assessment 505 | Stimulus Location Effectiveness Measures 507 ... |

| Client Cumulative Reports 511 | | |
|---|---|---|
| Media Grouped 513 | Campaign Grouped 515 | Time/Location Grouped 517 ... |

| Industry Cumulative And Syndicated Reports 521 | | | |
|---|---|---|---|
| Aggregate Assessment 523 | Top Performers 525 | Bottom Performers 527 | Outliers 529 | Trend 531 ... |

ANALYSIS OF CONTROLLED AND AUTOMATIC ATTENTION FOR INTRODUCTION OF STIMULUS MATERIAL

RELATED APPLICATIONS

This patent arises from a continuation of U.S. application Ser. No. 12/608,660 titled "Analysis of Controlled and Automatic Attention for Introduction of Stimulus Material," and filed on Oct. 29, 2009. U.S. application Ser. No. 12/608,660 is incorporated herein by this reference in its entirety.

This patent is related to U.S. patent application Ser. No. 12/056,190; U.S. patent application Ser. No. 12/056,211; U.S. patent application Ser. No. 12/056,221; U.S. patent application Ser. No. 12/056,225; U.S. patent application Ser. No. 12/113,863; U.S. patent application Ser. No. 12/113,870; U.S. patent application Ser. No. 12/122,240; U.S. patent application Ser. No. 12/122,253; U.S. patent application Ser. No. 12/122,262; U.S. patent application Ser. No. 12/135,066; U.S. patent application Ser. No. 12/135,074; U.S. patent application Ser. No. 12/182,851; U.S. patent application Ser. No. 12/182,874; U.S. patent application Ser. No. 12/199,557; U.S. patent application Ser. No. 12/199,583; U.S. patent application Ser. No. 12/199,596; U.S. patent application Ser. No. 12/200,813; U.S. patent application Ser. No. 12/234,372; U.S. patent application Ser. No. 12/135,069; U.S. patent application Ser. No. 12/234,388; U.S. patent application Ser. No. 12/544,921; U.S. patent application Ser. No. 12/544,958; U.S. patent application Ser. No. 12/546,586; U.S. patent application Ser. No. 12/410,380; U.S. patent application Ser. No. 12/410,372; U.S. patent application Ser. No. 12/413,297; U.S. patent application Ser. No. 12/545,455; U.S. patent application Ser. No. 12/544,934; U.S. patent application Ser. No. 12/608,685; U.S. patent application Ser. No. 13/444,149; U.S. patent application Ser. No. 12/608,696; U.S. patent application Ser. No. 12/731,868; U.S. patent application Ser. No. 13/045,457; U.S. patent application Ser. No. 12/778,810; U.S. patent application Ser. No. 12/778,828; U.S. patent application Ser. No. 13/104,821; U.S. patent application Ser. No. 13/104,840; U.S. patent application Ser. No. 12/846,242; U.S. patent application Ser. No. 12/853,197; U.S. patent application Ser. No. 12/884,034; U.S. patent application Ser. No. 12/868,531; U.S. patent application Ser. No. 12/913,102; U.S. patent application Ser. No. 12/853,213; U.S. patent application Ser. No. 13/105,774; U.S. patent application Ser. No. 13/569,711; U.S. patent application Ser. No. 13/708,525; U.S. patent application Ser. No. 13/708,344; U.S. patent application Ser. No. 13/730,511; U.S. patent application Ser. No. 13/730,550; U.S. patent application Ser. No. 13/730,541; U.S. patent application Ser. No. 13/730,564; U.S. patent application Ser. No. 13/965,805; U.S. patent application Ser. No. 13/945,357; and U.S. patent application Ser. No. 14/177,698.

FIELD OF THE DISCLOSURE

The present disclosure relates to analysis of controlled and automatic attention.

BACKGROUND

Conventional systems for placing stimulus material such as a media clip, product, brand image, message, purchase offer, product offer, etc., are limited. Some placement systems are based on demographic information, statistical data, and survey based response collection. However, conventional systems are subject to semantic, syntactic, metaphorical, cultural, and interpretive errors.

Consequently, it is desirable to provide improved methods and apparatus for introducing stimulus material.

BRIEF DESCRIPTION OF THE DRAWINGS

The disclosure may best be understood by reference to the following description taken in conjunction with the accompanying drawings, which illustrate particular examples.

FIG. 3 illustrates examples of data models that can be used with a stimulus and response repository.

DETAILED DESCRIPTION

Figure 1:
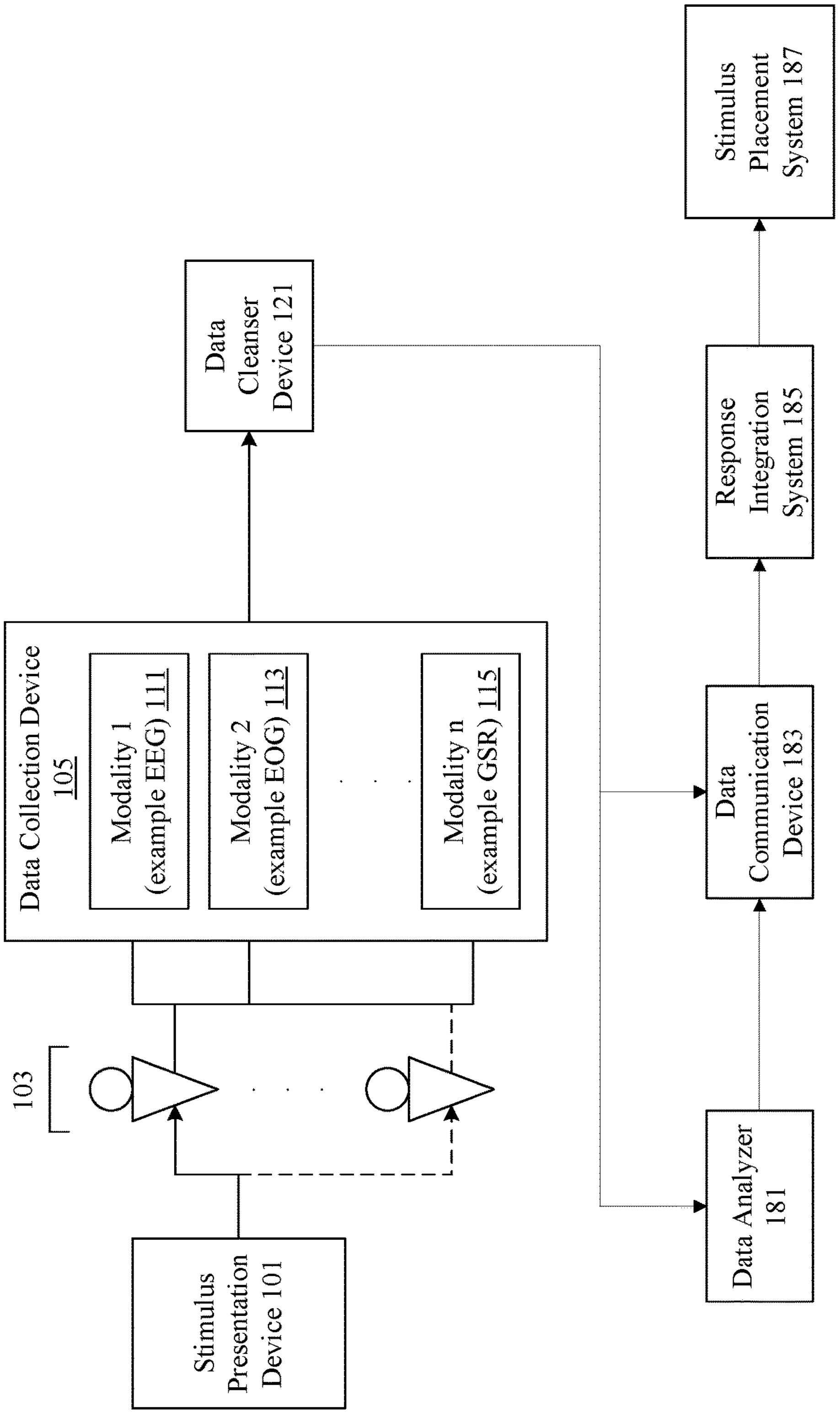
FIG. 1 illustrates one example of a system for neuro-response analysis.

Reference will now be made in detail to some specific examples of the disclosure including the best modes contemplated by the inventors for carrying out the disclosure. Examples are illustrated in the accompanying drawings. While the disclosure is described in conjunction with these specific examples, it will be understood that it is not intended to limit the disclosure to the described examples. On the contrary, it is intended to cover alternatives, modifications, and equivalents as may be included within the spirit and scope of the disclosure as defined by the appended claims.

For example, the techniques and mechanisms of the present disclosure will be described in the context of particular types of data such as central nervous system, autonomic nervous system, and effector data. However, it should be noted that the techniques and mechanisms of the present disclosure apply to a variety of different types of data. It should be noted that various mechanisms and techniques can be applied to any type of stimuli. In the following description, numerous specific details are set forth in order to provide a thorough understanding of the present disclosure. Particular examples may be implemented without some or all of these specific details. In other instances, well known process operations have not been described in detail in order not to unnecessarily obscure the present disclosure.

Various techniques and mechanisms of the present disclosure will sometimes be described in singular form for clarity. However, it should be noted that some examples include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

A system analyzes neuro-response measurements including regional electroencephalography (EEG) measurements from subjects exposed to stimulus materials to determine locations in stimulus materials eliciting controlled attention and automatic attention. Additional stimulus materials are inserted into locations having salient attention attributes. In some examples, a challenging task is used to direct controlled attention onto a location and additional stimulus material is subtly presented in the location to benefit from automatic attention and salient attention measurements.

Examples

Conventional placement systems such as product placement systems often rely on demographic information, statistical information, and survey based response collection to determine optimal locations to place stimulus material, such as a new product, a brand image, a video clip, sound files, etc. One problem with conventional stimulus placement systems is that conventional stimulus placement systems do not accurately measure the responses to components of the experience. They are also prone to semantic, syntactic, metaphorical, cultural, and interpretive errors thereby preventing the accurate and repeatable selection of stimulus placement locations.

Conventional systems do not use neuro-response measurements in evaluating spatial and temporal locations for personalized stimulus placement. The techniques and mechanisms of the present disclosure use neuro-response measurements such as central nervous system, autonomic nervous system, and effector measurements to improve stimulus location selection and stimulus personalization in video games. Some examples of central nervous system measurement mechanisms include Functional Magnetic Resonance Imaging (fMRI), Electroencephalography (EEG), and optical imaging. fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly. Even portable EEG with dry electrodes provides a large amount of neuro-response information.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

Many types of stimulus material may be placed into media. In some examples, brand images or messages are introduced into a movie or game. Text advertisements may be placed onto a prop in a video game scene or audio clips may be added to a music file. In some examples, a button to allow a player to purchase an item is provided in a neurologically salient location. Any type of stimulus material may be added to media materials such as movies, programs, texts, offers, games, etc.

However, stimulus material may often go unnoticed or may be ignored all together. Conventional mechanisms for eliciting user attention for stimulus materials in media materials are limited. According to various examples, a controlled and automatic attention analysis system analyzes media materials such as video games and video game scenes to determine candidate locations for introducing stimulus material. Each candidate location may be tagged with characteristics such as high retention placement, high attention location, good priming characteristics, etc. According to various examples, candidate locations are neurologically salient locations. When personalized stimulus is received, one of the candidate locations can be selected for placing the personalized stimulus material. Attention includes controlled attention and automatic attention. Regional EEG, particularly measurements in the frontal cortex, can be used to identify attention. If a search or task is difficult, the frontal cortex becomes involved. Saliency of attention can also be analyzed using EEG and/or other neuro-response mechanisms.

According to various examples, stimulus material is an advertisement or purchase offer tailored to a particular viewer. A controlled and automatic attention analysis mechanism may incorporate relationship assessments using brain regional coherence measures of segments of the stimuli relevant to the entity/relationship, segment effectiveness measures synthesizing the attention, emotional engagement and memory retention estimates based on the neurophysiological measures including time-frequency analysis of EEG measurements, and differential saccade related neural signatures during segments where coupling/relationship patterns are emerging in comparison to segments with non-coupled interactions. In particular examples, specific event related potential (ERP) analyses and/or event related power spectral perturbations (ERPSPs) are evaluated for different regions of the brain both before a subject is exposed to media materials to evaluated controlled and automatic attention and determine locations for introduction of stimulus materials. In particular examples, a task is used to direct a user's controlled attention toward a particular object and stimulus material is introduced at or near the particular object to elicit automatic attention.

Pre-stimulus and post-stimulus differential as well as target and distracter differential measurements of ERP time domain components at multiple regions of the brain are determined (DERP). Event related time-frequency analysis of the differential response to assess the attention, emotion and memory retention (DERPSPs) across multiple frequency bands including but not limited to theta, alpha, beta, gamma and high gamma is performed. In particular examples, single trial and/or averaged DERP and/or DERPSPs can be used to enhance selection of stimulus locations.

FIG. 1 illustrates one example of a system for performing controlled and automatic attention analysis system using neuro-response data. According to various examples, the stimulus location selection and personalization system includes a stimulus presentation device 101. In particular examples, the stimulus presentation device 101 is merely a display, monitor, screen, etc., that displays scenes of a video game to a user. Video games may include action, strategy, puzzle, simulation, role-playing, and other computer games. The stimulus presentation device 101 may also include one or more controllers used to control and interact with aspects of the video game. Controllers may include keyboards, steering wheels, motion controllers, touchpads, joysticks, control pads, etc.

According to various examples, the subjects 103 are connected to data collection devices 105. The data collection devices 105 may include a variety of neuro-response measurement mechanisms including neurological and neurophysiological measurements systems such as EEG, EOG, GSR, EKG, pupillary dilation, eye tracking, facial emotion encoding, and reaction time devices, etc. According to various examples, neuro-response data includes central nervous system, autonomic nervous system, and effector data. In particular examples, the data collection devices 105 include EEG 111, EOG 113, and GSR 115. In some instances, only a single data collection device is used. Data collection may proceed with or without human supervision.

The data collection device 105 collects neuro-response data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular examples, data collected is digitally sampled and stored for later analysis. In particular examples, the data collected could be analyzed in real-time. According to particular examples, the digital sampling rates are adaptively chosen based on the neurophysiological and neurological data being measured.

In one particular examples, the stimulus location selection system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular examples, the data collection devices are clock synchronized with a stimulus presentation device 101. In particular examples, the data collection devices 105 also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. According to various examples, the data collection devices include mechanisms for not only monitoring subject neuro-response to stimulus materials, but also include mechanisms for identifying and monitoring the stimulus materials. For example, data collection devices 105 may be synchronized with a set-top box to monitor channel changes. In other examples, data collection devices 105 may be directionally synchronized to monitor when a subject is no longer paying attention to stimulus material. In still other examples, the data collection devices 105 may receive and store stimulus material generally being viewed by the subject, whether the stimulus is a program, a commercial, printed material, an experience, or a scene outside a window. The data collected allows analysis of neuro-response information and correlation of the information to actual stimulus material and not mere subject distractions.

According to various examples, the stimulus location selection system also includes a data cleanser device 121. In particular examples, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various examples, the data cleanser device 121 is implemented using hardware, firmware, and/or software. It should be noted that although a data cleanser device 121 is shown located after a data collection device 105 and before data analyzer 181, the data cleanser device 121 like other components may have a location and functionality that varies based on system implementation. For example, some systems may not use any automated data cleanser device whatsoever while in other systems, data cleanser devices may be integrated into individual data collection devices.

According to various examples, an optional stimulus attributes repository 131 provides information on the stimulus material being presented to the multiple subjects. According to various examples, stimulus attributes include properties of the stimulus materials as well as purposes, presentation attributes, report generation attributes, etc. In particular examples, stimulus attributes include time span, channel, rating, media, type, etc. Stimulus attributes may also include positions of entities in various frames, components, events, object relationships, locations of objects and duration of display. Purpose attributes include aspiration and objects of the stimulus including excitement, memory retention, associations, etc. Presentation attributes include audio, video, imagery, and messages needed for enhancement or avoidance. Other attributes may or may not also be included in the stimulus attributes repository or some other repository.

The data cleanser device 121 and the stimulus attributes repository 131 pass data to the data analyzer 181. The data analyzer 181 uses a variety of mechanisms to analyze underlying data in the system to place stimulus. According to various examples, the data analyzer customizes and extracts the independent neurological and neuro-physiological parameters for each individual in each modality, and blends the estimates within a modality as well as across modalities to elicit an enhanced response to the presented stimulus material. In particular examples, the data analyzer 181 aggregates the response measures across subjects in a dataset.

According to various examples, neurological and neurophysiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to various examples, the data analyzer 181 may include an intra-modality response synthesizer and a cross-modality response synthesizer. In particular examples, the intra-modality response synthesizer is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset.

According to various examples, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various examples, the data analyzer 181 also includes a composite enhanced effectiveness estimator (CEEE) that combines the enhanced responses and estimates from each modality to provide a blended estimate of the effectiveness. In particular examples, blended estimates are provided for each exposure of a subject to stimulus materials. The blended estimates are evaluated over time to assess stimulus location characteristics. According to various examples, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to various examples, the data analyzer 181 provides analyzed and enhanced response data to a data communication device 183. It should be noted that in particular instances, a data communication device 183 is not necessary. According to various examples, the data communication device 183 provides raw and/or analyzed data and insights. In particular examples, the data communication device 183 may include mechanisms for the compression and encryption of data for secure storage and communication.

According to various examples, the data communication device 183 transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various examples, the data communication device is a set top box, wireless device, computer system, etc. that transmits data obtained from a data collection device to a response integration system. In particular examples, the data communication device may transmit data even before data cleansing or data analysis. In other examples, the data communication device may transmit data after data cleansing and analysis.

In particular examples, the data communication device 183 sends data to a response integration system 185. According to various examples, the response integration system 185 assesses and extracts controlled and automatic attention characteristics. In particular examples, the response integration system 185 determines entity positions in various stimulus segments and matches position information with eye tracking paths while correlating saccades with neural assessments of attention, memory retention, and emotional engagement. In particular examples, the response integration system 185 also collects and integrates user behavioral and survey responses with the analyzed response data to more effectively select stimulus locations.

A variety of data can be stored for later analysis, management, manipulation, and retrieval. In particular examples, the repository could be used for tracking stimulus attributes and presentation attributes, audience responses and optionally could also be used to integrate audience measurement information.

As with a variety of the components in the system, the response integration system can be co-located with the rest of the system and the user, or could be implemented in a remote location. It could also be optionally separated into an assessment repository system that could be centralized or distributed at the provider or providers of the stimulus material. In other examples, the response integration system is housed at the facilities of a third party service provider accessible by stimulus material providers and/or users. A stimulus placement system 187 identifies temporal and spatial locations along with personalized material for introduction into the stimulus material. The personalized stimulus material introduced into a video game can be reintroduced to check the effectiveness of the placements.

Figure 2:
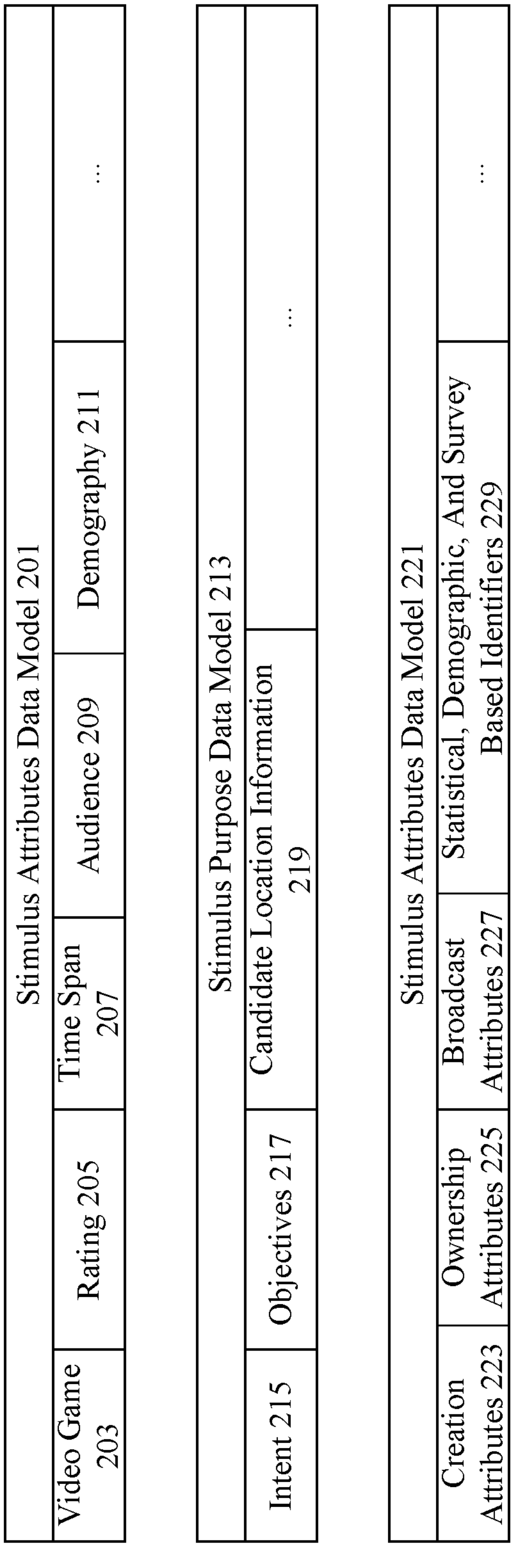
FIG. 2 illustrates examples of stimulus attributes that can be included in a stimulus attributes repository.

FIG. 2 illustrates examples of data models that may be provided with a stimulus attributes repository. According to various examples, a stimulus attributes data model 201 includes a video game 203, rating 205, time span 207, audience 209, and demographic information 211. A stimulus purpose data model 213 may include intents 215 and objectives 217. According to various examples, stimulus attributes data model 201 also includes candidate location information 219 about various temporal, spatial, activity, and event components in an experience that may hold stimulus material. For example, a video game may show a blank wall included on some scenes that can be used to display an advertisement. The temporal and spatial characteristics of the blank wall may be provided in candidate location information 219.

According to various examples, another stimulus attributes data model 221 includes creation attributes 223, ownership attributes 225, broadcast attributes 227, and statistical, demographic and/or survey based identifiers 229 for automatically integrating the neuro-physiological and neuro-behavioral response with other attributes and meta-information associated with the stimulus.

FIG. 3 illustrates examples of data models that can be used for storage of information associated with selection of locations for the introduction of stimulus material. According to various examples, a dataset data model 301 includes an experiment name 303 and/or identifier, client attributes 305, a subject pool 307, logistics information 309 such as the location, date, and time of testing, and stimulus material 311 including stimulus material attributes.

In particular examples, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

According to various examples, data models for neuro-feedback association 325 identify experimental protocols 327, modalities included 329 such as EEG, EOG, GSR, surveys conducted, and experiment design parameters 333 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 337. According to various examples, the data collection data model 337 includes recording attributes 339 such as station and location identifiers, the data and time of recording, and operator details. In particular examples, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various examples, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

Figure 4:
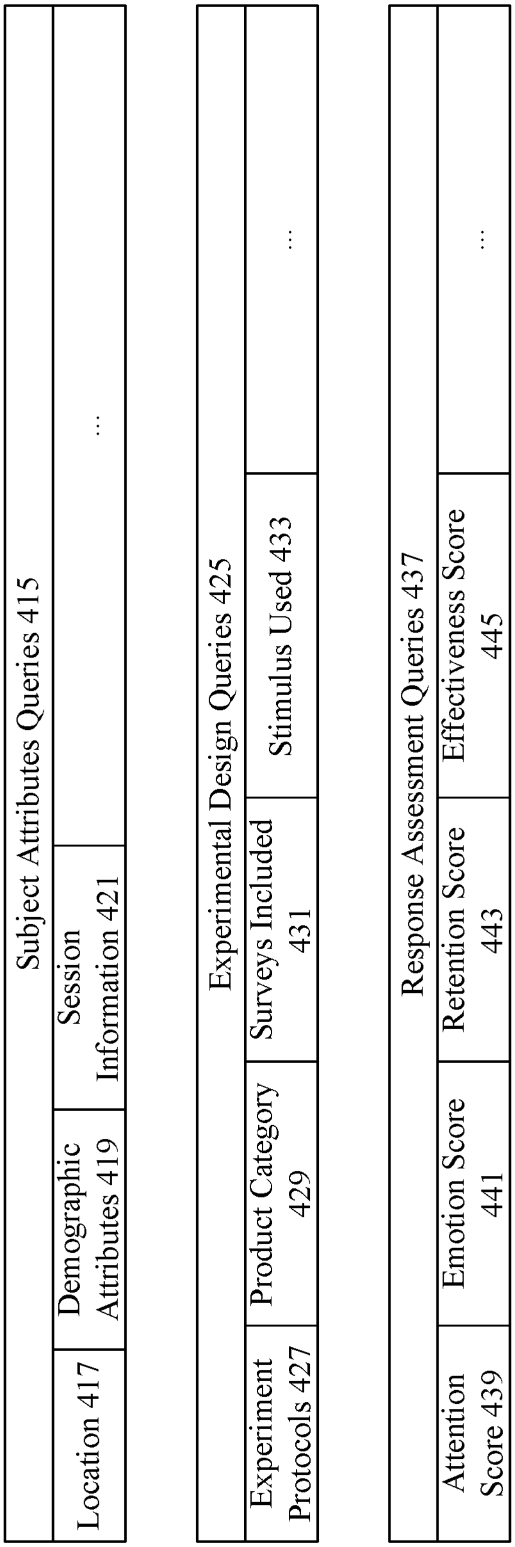
FIG. 4 illustrates one example of a query that can be used with a stimulus location selection system.

FIG. 4 illustrates examples of queries that can be performed to obtain data associated with stimulus location selection and analysis of controlled and automatic attention. For example, users may query to determine what types of consumers respond most to a particular experience or component of an experience. According to various examples, queries are defined from general or customized scripting languages and constructs, visual mechanisms, a library of preset queries, diagnostic querying including drill-down diagnostics, and eliciting what if scenarios. According to various examples, subject attributes queries 415 may be configured to obtain data from a neuro-informatics repository using a location 417 or geographic information, session information 421 such as testing times and dates, and demographic attributes 419. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries 425 may obtain data from a neuro-informatics repository based on experiment protocols 427, product category 429, surveys included 431, and stimulus provided 433. Other fields that may be used include the number of protocol repetitions used, combination of protocols used, and usage configuration of surveys.

Client and industry based queries may obtain data based on the types of industries included in testing, specific categories tested, client companies involved, and brands being tested. Response assessment based queries 437 may include attention scores 439, emotion scores, 441, retention scores 443, and effectiveness scores 445. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

Figure 5:
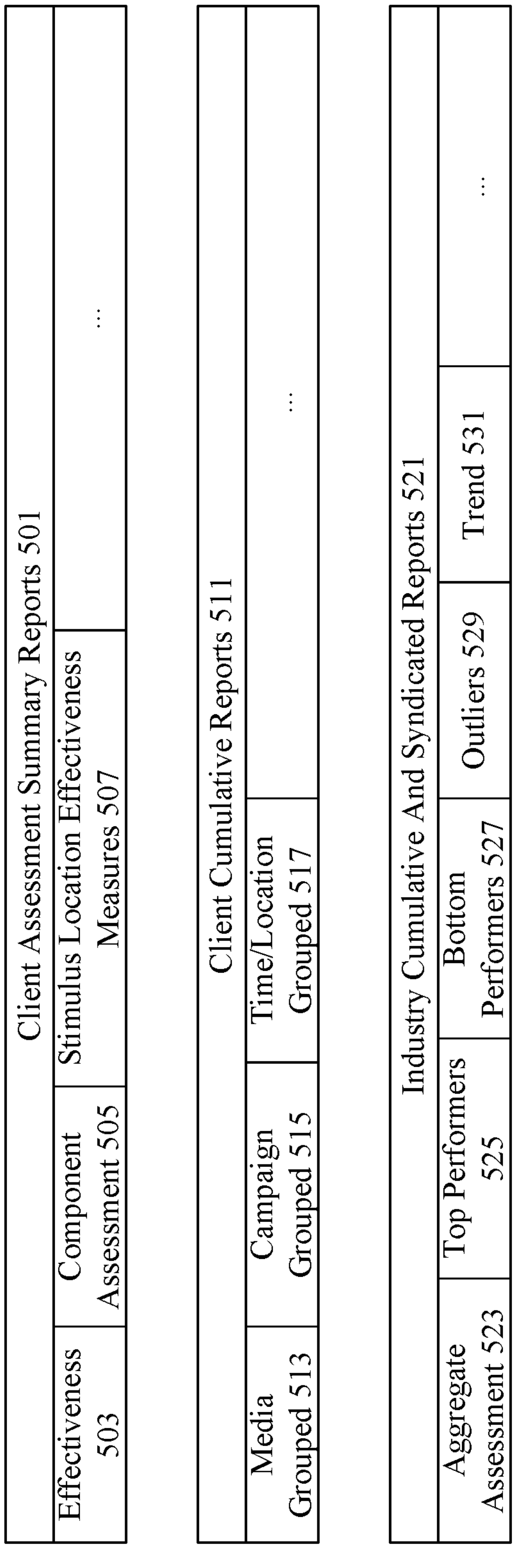
FIG. 5 illustrates one example of a report generated using the automatic and controlled attention analysis system.

FIG. 5 illustrates examples of reports that can be generated. According to various examples, client assessment summary reports 501 include effectiveness measures 503, component assessment measures 505, and stimulus location effectiveness measures 507. Effectiveness assessment measures include composite assessment measure(s), industry/category/client specific placement (percentile, ranking, etc.), actionable grouping assessment such as removing material, modifying segments, or fine tuning specific elements, etc., and the evolution of the effectiveness profile overtime. In particular examples, component assessment reports include component assessment measures like attention, emotional engagement scores, percentile placement, ranking, etc. Component profile measures include time based evolution of the component measures and profile statistical assessments. According to various examples, reports include the number of times material is assessed, attributes of the multiple presentations used, evolution of the response assessment measures over the multiple presentations, and usage recommendations.

According to various examples, client cumulative reports 511 include media grouped reporting 513 of all stimulus assessed, campaign grouped reporting 515 of stimulus assessed, and time/location grouped reporting 517 of stimulus assessed. According to various examples, industry cumulative and syndicated reports 521 include aggregate assessment responses measures 523, top performer lists 525, bottom performer lists 527, outliers 529, and trend reporting 531. In particular examples, tracking and reporting includes specific products, categories, companies, brands.

Figure 6:
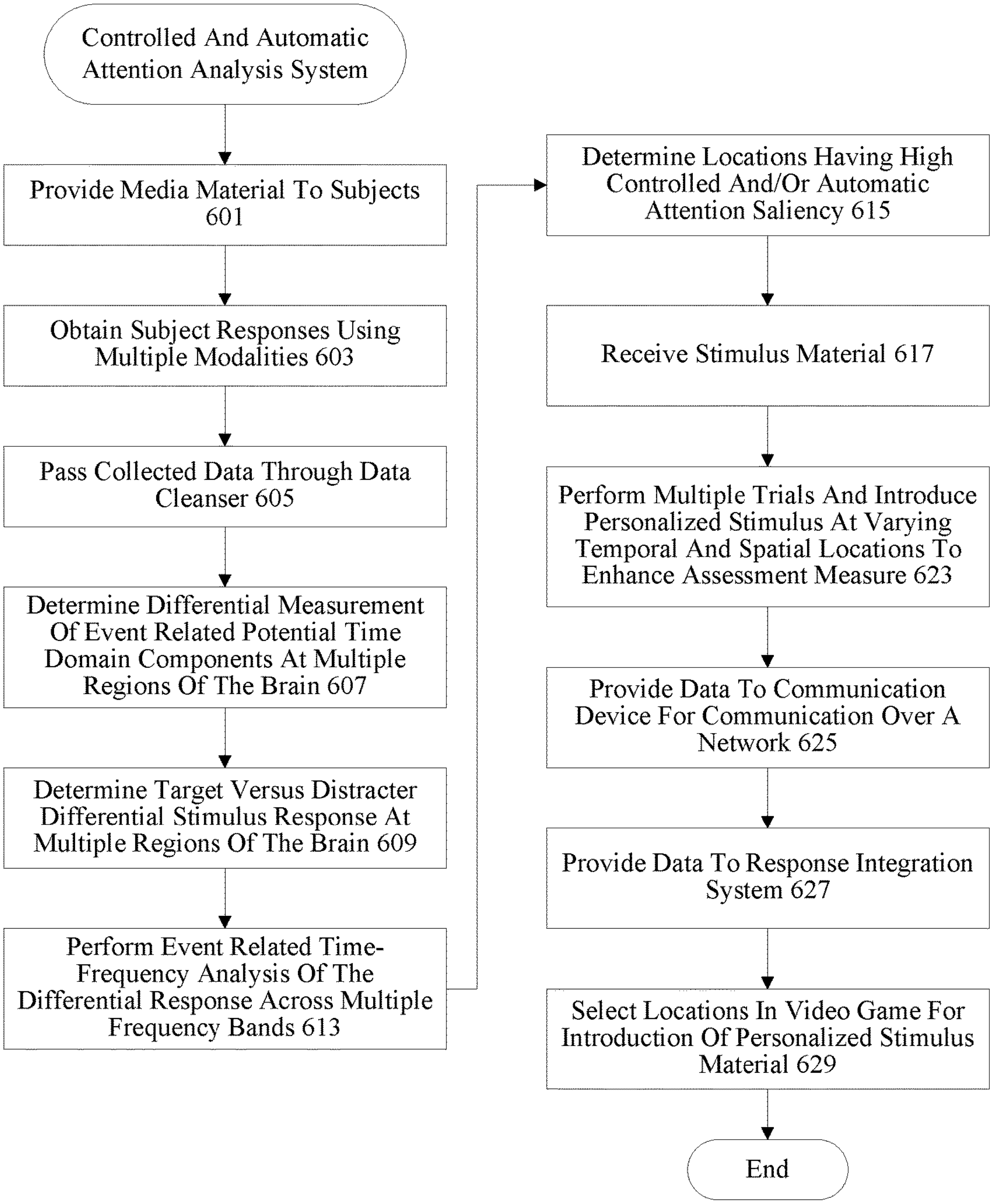
FIG. 6 illustrates one example of a technique for performing automatic and controlled attention location assessment.

FIG. 6 illustrates one example of stimulus location selection using analysis of controlled and automatic attention. At 601, stimulus material is provided to multiple subjects in multiple geographic markets. According to various examples, stimulus is a video game. At 603, subject responses are collected using a variety of modalities, such as EEG, ERP, EOG, GSR, etc. In some examples, verbal and written responses can also be collected and correlated with neurological and neurophysiological responses. In other examples, data is collected using a single modality. At 605, data is passed through a data cleanser to remove noise and artifacts that may make data more difficult to interpret. According to various examples, the data cleanser removes EEG electrical activity associated with blinking and other endogenous/exogenous artifacts.

According to various examples, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis. In particular examples, a stimulus attributes repository is accessed to obtain attributes and characteristics of the stimulus materials, along with purposes, intents, objectives, etc. In particular examples, EEG response data is synthesized to provide an enhanced assessment of effectiveness. According to various examples, EEG measures electrical activity resulting from thousands of simultaneous neural processes associated with different portions of the brain. EEG data can be classified in various bands. According to various examples, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present disclosure recognize that analyzing high gamma band (kappa-band: Above 60 Hz) measurements, in addition to theta, alpha, beta, and low gamma band measurements, enhances neurological attention, emotional engagement and retention component estimates. In particular examples, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various examples, high gamma waves (kappa-band) above 80 Hz (typically detectable with sub-cranial EEG and/or magnetoencephalography) can be used in inverse model-based enhancement of the frequency responses to the stimuli.

Various examples of the present disclosure recognize that particular sub-bands within each frequency range have particular prominence during certain activities. A subset of the frequencies in a particular band is referred to herein as a sub-band. For example, a sub-band may include the 40-45 Hz range within the gamma band. In particular examples, multiple sub-bands within the different bands are selected while remaining frequencies are band pass filtered. In particular examples, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various examples, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various examples, data from a specific modality can be enhanced using data from one or more other modalities. In particular examples, EEG typically makes frequency measurements in different bands like alpha, beta and gamma to provide estimates of significance. However, the techniques of the present disclosure recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various examples, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various examples, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various examples, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular examples, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various examples, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular examples, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various examples, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various examples, facial emotion encoding uses templates generated by measuring facial muscle positions and movements of individuals expressing various emotions prior to the testing session. These individual specific facial emotion encoding templates are matched with the individual responses to identify subject emotional response. In particular examples, these facial emotion encoding measurements are enhanced by evaluating inter-hemispherical asymmetries in EEG responses in specific frequency bands and measuring frequency band interactions. The techniques of the present disclosure recognize that not only are particular frequency bands significant in EEG responses, but particular frequency bands used for communication between particular areas of the brain are significant. Consequently, these EEG responses enhance the EMG, graphic and video based facial emotion identification.

According to various examples, post-stimulus versus pre-stimulus differential measurements of ERP time domain components in multiple regions of the brain (DERP) are measured at 607. The differential measures give a mechanism for eliciting responses attributable to the stimulus. For example the messaging response attributable to an ad or the brand response attributable to multiple brands is determined using pre-experience and post-experience estimates At 609, target versus distracter stimulus differential responses are determined for different regions of the brain (DERP). At 613, event related time-frequency analysis of the differential response (DERPSPs) are used to assess the attention, emotion and memory retention measures across multiple frequency bands. According to various examples, the multiple frequency bands include theta, alpha, beta, gamma and high gamma or kappa.

At 615, locations having high controlled and/or automatic attention saliency are identified. According to various examples, candidate locations may include areas immediately following a sequence of salient controlled attention. Candidate locations may include locations where a user has high anticipation or is in a state of high awareness. Alternatively, locations where a user is sufficiently primed may be selected for particular messages and placements. In other examples, neuro-response lulls in source material are identified.

Locations having little change in relation to neighboring locations may also be selected. In still other examples, locations are manually selected. At 617, stimulus material is received. According to various examples, stimulus material may include presentations, messages, banners, videos, audio, etc. In particular examples, a controlled and automatic attention analysis system determines neurologically effective locations to place the message.

For example, the message may be placed where a user will be directing maximum attention. In one example, the message may be shown when a hero is about to enter a room for a final confrontation. At 623, multiple trials are performed with stimulus material introduced in different spatial and temporal locations to assess the impact of introduction at each of the different spatial and temporal locations.

For example, introduction of new products at location A on a billboard in a video game scene may lead to more significant neuro-response activity for the billboard in general. Introduction of an image onto a video stream may lead to greater emotional engagement and memory retention. In other examples, increased neuro-response activity for introduced material may detract from neuro-response activity for other portions of source material. For examples, a salient image on one part of a billboard may lead to reduced dwell times for other portions of a billboard. According to various examples, aggregated neuro-response measurements are identified to determine optimal locations for introduction of stimulus material.

At 625, processed data is provided to a data communication device for transmission over a network such as a wireless, wireline, satellite, or other type of communication network capable of transmitting data. Data is provided to response integration system at 627. According to various examples, the data communication device transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various examples, data is sent using a telecommunications, wireless, Internet, satellite, or any other communication mechanisms that is capable of conveying information from multiple subject locations for data integration and analysis. The mechanism may be integrated in a set top box, computer system, receiver, mobile device, etc.

In particular examples, the data communication device sends data to the response integration system 627. According to various examples, the response integration system 627 combines the analyzed responses to the experience/stimuli, with information on the available stimuli and its attributes. A variety of responses including user behavioral and survey responses are also collected an integrated. At 629, one or more locations in the video game are selected for the introduction of personalized stimulus material.

According to various examples, the response integration system combines analyzed and enhanced responses to the stimulus material while using information about stimulus material attributes such as the location, movement, acceleration, and spatial relationships of various entities and objects. In particular examples, the response integration system also collects and integrates user behavioral and survey responses with the analyzed and enhanced response data to more effectively assess stimulus location characteristics.

According to various examples, the stimulus location selection system provides data to a repository for the collection and storage of demographic, statistical and/or survey based responses to different entertainment, marketing, advertising and other audio/visual/tactile/olfactory material. If this information is stored externally, this system could include a mechanism for the push and/or pull integration of the data—including but not limited to querying, extracting, recording, modifying, and/or updating. This system integrates the requirements for the presented material, the assessed neuro-physiological and neuro-behavioral response measures, and the additional stimulus attributes such as demography/statistical/survey based responses into a synthesized measure for the selection of stimulus locations.

According to various examples, the repository stores information for temporal, spatial, activity, and event based components of stimulus material. For example, neuro-response data, statistical data, survey based response data, and demographic data may be aggregated and stored and associated with a particular component in a video stream.

Figure 7:
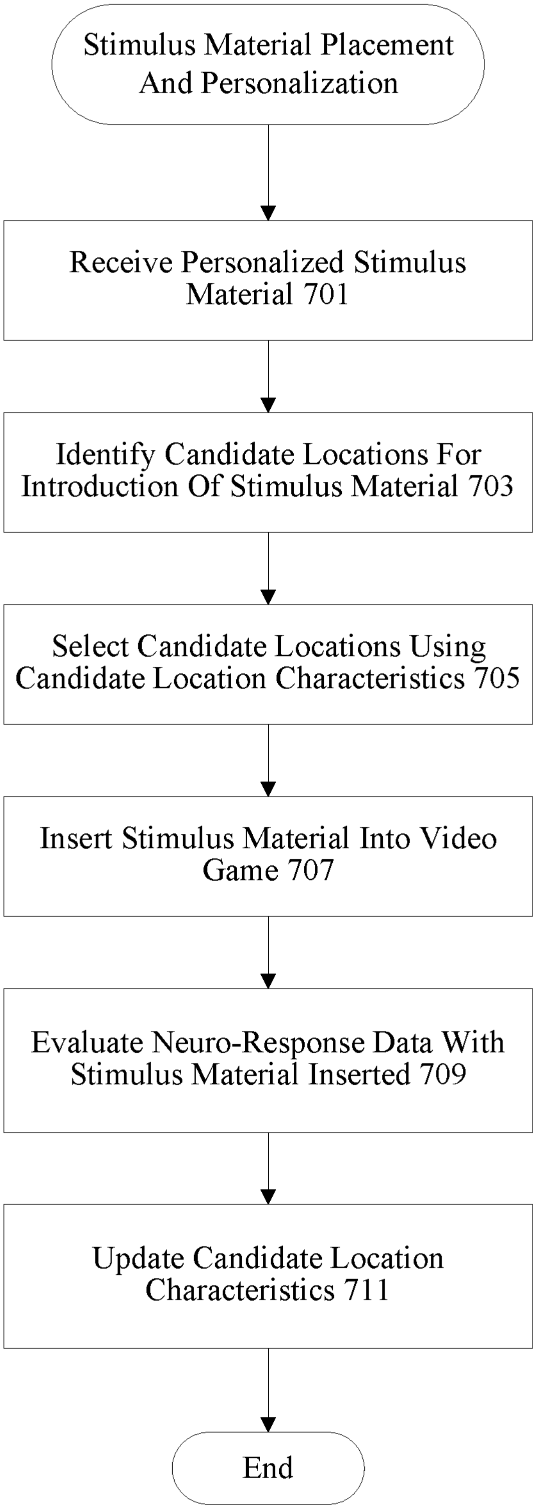
FIG. 7 illustrates one example of technique for introducing additional stimulus materials.

FIG. 7 illustrates an example of a technique for controlled and automatic attention analysis. According to various examples, additional stimulus material is received at 701. In particular examples, stimulus material may be video, audio, text, banners, messages, product offers, purchase offers, etc. At 703, candidate locations for introduction of stimulus material are identified. Candidate locations may be predetermined and provided with the media material such as the movie or video game itself. In particular examples, candidate locations are selected using neuro-response data to determine effective candidate locations for insertion of stimulus material. According to particular examples, candidate locations are locations having high controlled and/or automatic attention metrics. In other examples, candidate locations are neurologically salient locations for the introduction of advertisements, messages, purchase icons, media, offers, etc. In some examples, both personalized and non-personalized stimulus material may be inserted.

According to various examples, candidate locations are selected based on candidate location characteristics 705. For example, candidate location characteristics may indicate that some locations have particularly good memory and retention characteristics. In other examples, candidate location characteristics may indicate that a particular sport has good attention attributes. According to various examples, particular locations may indicate good priming for particular types of material, such as a category of ads or a type of message. According to various examples, particular events may also trigger stimulus material insertion. For example, if a player moves into first place into a racing game, a message or other stimulus material may be shown to the user. Stimulus material placement in video games may be spatial and temporal location driven or event driven. At 707, stimulus material is inserted into the video game. At 709, neuro-response data is evaluated with stimulus material inserted. In some examples, EEG data may be available. However, in other examples, little or no neuro-response data may be available. Only user activity or user facial expressions or user feedback may be available.

At 711, characteristics associated with candidate locations are updated based on user feedback. The location and placement assessment system can further include an adaptive learning component that refines profiles and tracks variations responses to particular stimuli or series of stimuli over time.

Figure 8:
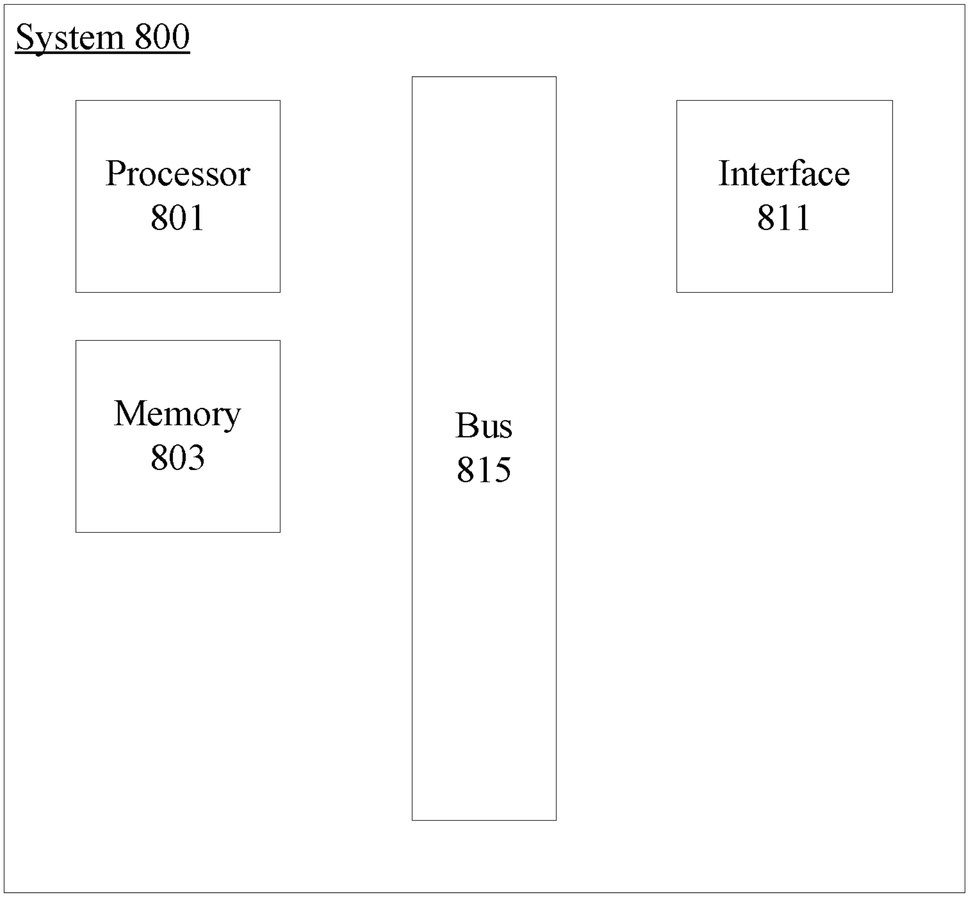
FIG. 8 provides one example of a system that can be used to implement one or more mechanisms.

According to various examples, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system. FIG. 8 provides one example of a system that can be used to implement one or more mechanisms. For example, the system shown in FIG. 8 may be used to implement a stimulus location selection system.

According to particular examples, a system 800 suitable for implementing particular examples of the present disclosure includes a processor 801, a memory 803, an interface 811, and a bus 815 (e.g., a PCI bus). When acting under the control of appropriate software or firmware, the processor 801 is responsible for such tasks such as pattern generation. Various specially configured devices can also be used in place of a processor 801 or in addition to processor 801. The complete implementation can also be done in custom hardware. The interface 811 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular examples, the system 800 uses memory 803 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present disclosure relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing disclosure has been described in some detail for purposes of clarity of understanding, it will be apparent that certain changes and modifications may be practiced within the scope of the appended claims. Therefore, the present embodiments are to be considered as illustrative and not restrictive and the disclosure is not to be limited to the details given herein, but may be modified within the scope and equivalents of the appended claims.

What is claimed is:

1. A system comprising:

an analyzer to:

identify a first event in first neuro-response data gathered from a user while the user is exposed to media and a second event in the first neuro-response data;

correlate a first location in the media with the first event and a second location in the media with the second event;

determine a first user resonance of the user at the first location based on the first event; and determine a second user resonance of the user at the second location based on the second event; and a selector to select a third location in the media after the first location or a fourth location in the media after the second location as a candidate location for introduction of advertising material based on the first user resonance and the second user resonance, the selector to select the candidate location by selecting the third location when the first user resonance is increased relative to the second user resonance and by selecting the fourth location when the second user resonance is increased relative to the first user resonance.

2. The system of claim 1, wherein the third location and the fourth location are one of a temporal location in the media or a spatial location in the media.

3. The system of claim 1, wherein the first event is a change in amplitude in the first neuro-response data.

4. The system of claim 1, wherein the analyzer is to determine a first controlled attention level of the user at the first location based on the first neuro-response data and determine a second controlled attention level of the user at the second location based on the first neuro-response data, and wherein the selector is to further select the third location or the fourth location as the candidate location based on the first controlled attention level and the second controlled attention level.

5. The system of claim 1, wherein the analyzer is to:

determine an automatic attention level of the user based on second neuro-response data gathered from the user while the user is exposed to the advertising material in the candidate location; and determine an effectiveness of the advertising material in the candidate location based on the automatic attention level.

6. The system of claim 1, wherein the analyzer is to:

determine a first controlled attention level of the user based on second neuro-response data gathered from the user while the user is exposed to the advertising material in the candidate location;

determine a second controlled attention level of the user based on third neuro-response data gathered from the user while the user is exposed to media at a fifth location in the media; and perform a comparison of the first controlled attention level and the second controlled attention level, the selector to one of maintain the selection of the candidate location or modify the selection of the candidate location based on the comparison.

7. The system of claim 1, wherein the analyzer is to:

analyze second neuro-response data gathered from the user while the user is exposed to media in the third location and third neuro-response data gathered from the user while the user is exposed media in the fourth location; and perform a comparison of (1) the first neuro-response data and the second neuro-response data and (2) the first neuro-response data and the third neuro-response data, the selector to further select the one of the third location or the fourth location as the candidate location based on the comparison.

8. A method comprising:

identifying, by executing an instruction with a processor, a first event in first neuro-response data gathered from a user while the user is exposed to media and a second event in the first neuro-response data;

correlating, by executing an instruction with the processor, a first location in the media with the first event and a second location in the media with the second event;

determining, by executing an instruction with the processor, a first user resonance of the user at the first location based on the first event;

determining, by executing an instruction with the processor, a second user resonance of the user at the second location based on the second event; and selecting, by executing an instruction with the processor, a third location in the media after the first location or a fourth location in the media after the second location as a candidate location for introduction of advertising material based on the first user resonance and the second user resonance, the third location to be selected as the candidate location when the first user resonance is increased relative to the second user resonance and the fourth location to be selected as the candidate location when the second user resonance is increased relative to the first user resonance.

9. The method of claim 8, wherein the third location and the fourth location are one of a temporal location in the media or a spatial location in the media.

10. The method of claim 8, wherein the first event is a change in amplitude in the first neuro-response data.

11. The method of claim 8, further including:

determining a first controlled attention level of the user at the first location based on the first neuro-response data; and determining a second controlled attention level of the user at the second location based on the first neuro-response data, wherein the selecting of the third location or the fourth location as the candidate location is further based on the first controlled attention level and the second controlled attention level.

12. The method of claim 8, further including:

determining an automatic attention level of the user based on second neuro-response data gathered from the user while the user is exposed to the advertising material in the candidate location; and determining an effectiveness of the advertising material in the candidate location based on the automatic attention level.

13. The method of claim 8, further including:

determining a first controlled attention level of the user based on second neuro-response data gathered from the user while the user is exposed to the advertising material in the candidate location;

determining a second controlled attention level of the user based on third neuro-response data gathered from a user while the user is exposed to media at a fifth location in the media;

performing a comparison of the first controlled attention level and the second controlled attention level; and maintaining the selection of the candidate location or modifying the selection of the candidate location based on the comparison.

14. The method of claim 8, further including:

analyzing second neuro-response data gathered from the user while the user is exposed to media in the third location and third neuro-response data gathered from the user while the user is exposed media in the fourth location;

performing a comparison of (1) the first neuro-response data and the second neuro-response data and (2) the first neuro-response data and the third neuro-response data; and selecting the one of the third location or the fourth location as the candidate location based on the comparison.

15. A tangible machine readable storage device or storage disc comprising instructions which, when executed by a machine, cause the machine to at least:

identify a first event in first neuro-response data gathered from a user while the user is exposed to media and a second event in the first neuro-response data;

correlate a first location in the media with the first event and a second location in the media with the second event;

determine a first user resonance of the user at the first location based on the first event;

determine a second user resonance of the user at the second location based on the second event; and select a third location in the media after the first location or a fourth location in the media after the second location as a candidate location for introduction of advertising material based on the first user resonance and the second user resonance, the third location to be selected as the candidate location when the first user resonance is increased relative to the second user resonance and the fourth location to be selected as the candidate location when the second user resonance is increased relative to the first user resonance.

16. The storage device or storage disc of claim 15, wherein the third location and the fourth location are one of a temporal location in the media or a spatial location in the media.

17. The storage device or storage disc of claim 15, wherein the first event is a change in amplitude in the first neuro-response data.

18. The storage device or storage disc of claim 15, wherein the instructions cause the machine to:

determine a first controlled attention level of the user at the first location based on the first neuro-response data; and determine a second controlled attention level of the user at the second location based on the first neuro-response data, the machine to further select the third location or the fourth location as the candidate location based on the first controlled attention level and the second controlled attention level.

19. The storage device or storage disc of claim 15, wherein the instructions cause the machine to:

determine an automatic attention level of the user based on second neuro-response data gathered from the user while the user is exposed to the advertising material in the candidate location; and determine an effectiveness of the advertising material in the candidate location based on the automatic attention level.

20. The storage device or storage disc of claim 15, wherein the instructions cause the machine to:

determine a first controlled attention level of the user based on second neuro-response data gathered from the user while the user is exposed to the advertising material in the candidate location;

determine a second controlled attention level of the user based on third neuro-response data gathered from a user while the user is exposed to media at a fifth location in the media;

perform a comparison of the first controlled attention level and the second controlled attention level; and maintain the selection of the candidate location or modify the selection of the candidate location based on the comparison.

* * * * *